United States Patent
Jackowski et al.

(10) Patent No.: US 9,248,138 B2
(45) Date of Patent: *Feb. 2, 2016

(54) PROCESS AND COMPOSITION FOR STABILIZATION OF VULNERABLE PLAQUE UTILIZING A COMBINATION OF A STATIN AND OMEGA 3 FATTY ACIDS

(71) Applicant: PIVOTAL THERAPEUTICS INC., Woodbridge (CA)

(72) Inventors: George Jackowski, King (CA); Rachelle MacSweeney, King (CA); Nisar Ahmad Shaikh, Mississauga (CA); Jason Yantha, Brampton (CA); Valerie B. Schini-Kerth, Fessenheim-le-Bas (FR)

(73) Assignee: Pivotal Therapeutics, Inc., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/594,095

(22) Filed: Jan. 10, 2015

(65) Prior Publication Data

US 2015/0196571 A1    Jul. 16, 2015

Related U.S. Application Data

(63) Continuation-in-part of application No. 13/584,480, filed on Aug. 13, 2012, now Pat. No. 8,951,514, which is a continuation-in-part of application No. PCT/US2012/025026, filed on Feb. 14, 2012.

(60) Provisional application No. 61/925,692, filed on Jan. 10, 2014, provisional application No. 61/457,267, filed on Feb. 16, 2011.

(51) Int. Cl.
| | |
|---|---|
| *A61K 31/662* | (2006.01) |
| *A61K 31/505* | (2006.01) |
| *A61K 31/4418* | (2006.01) |
| *A61K 31/47* | (2006.01) |
| *A61K 31/40* | (2006.01) |
| *A61K 31/404* | (2006.01) |
| *A61K 31/366* | (2006.01) |
| *A61K 31/22* | (2006.01) |
| *A61K 31/232* | (2006.01) |

(52) U.S. Cl.
CPC .............. *A61K 31/662* (2013.01); *A61K 31/22* (2013.01); *A61K 31/232* (2013.01); *A61K 31/366* (2013.01); *A61K 31/40* (2013.01); *A61K 31/404* (2013.01); *A61K 31/4418* (2013.01); *A61K 31/47* (2013.01); *A61K 31/505* (2013.01)

(58) Field of Classification Search
None
See application file for complete search history.

*Primary Examiner* — Karl J Puttlitz
(74) *Attorney, Agent, or Firm* — Ferris H. Lander, Inc.

(57) ABSTRACT

A composition and a method of treatment utilizing a combination of statins (or HMG-CoA reductase inhibitors), a class of drug used to lower cholesterol levels by inhibiting the enzyme HMG-CoA reductase, with mixtures of an omega-3 fatty acid formulation containing about 90% or more omega 3 fatty acids by weight including a combination of Eicosapentaenoic acid (EPA), Docosapentaenoic acid (DPA) and Docosahexaenoic acid (DHA) in a weight ratio of EPA:DHA of from 5.7 to 6.3, wherein the sum of the EPA, DHA and DPA represent about 82% by weight of the total formulation and about 92% of the total omega 3 fatty acid content of the composition, the compositions and method designed to stabilize vulnerable plaque while mediating omega-3 deficiencies in individuals in need thereof.

13 Claims, 15 Drawing Sheets

PROCESS AND COMPOSITION FOR STABILIZATION OF VULNERABLE PLAQUE UTILIZING A COMBINATION OF A STATIN AND OMEGA 3 FATTY ACIDS

CROSS-REFERENCE TO RELATED APPLICATIONS

This application is a continuation-in-part of U.S. application Ser. No. 13/584,480, filed Aug. 13, 2012, now U.S. Pat. No. 8,951,514, issued Feb. 10, 2015, which is a continuation-in-part of PCT/US 2012/025026, filed Feb. 14, 2012, which claims benefit of priority to U.S. Provisional Patent Application Ser. No. 61/457,267, filed Feb. 16, 2011.

This application further claims benefit of priority to U.S. Provisional Patent Application Ser. No. 61/925,692, filed Jan. 10, 2014.

The contents of the above-referenced applications are incorporated herein by reference in their entireties.

FIELD OF THE INVENTION

The present invention relates to combinations of one or more statins (or HMG-CoA reductase inhibitors), a class of drug used to lower cholesterol levels by inhibiting the enzyme HMG-CoA reductase, with mixtures of omega-3 fatty acid compositions designed to stabilize vulnerable plaque while mediating omega-3 deficiencies in individuals in need thereof; and to methods of administering such combinations, and to unit dosages of such combinations for the reduction of apolipoprotein-B levels in cardiovascular disease patients (CVD). The invention particularly relates to compositions wherein the omega-3 formulation is designed to mediate omega-3 deficiencies in individuals in need thereof by elevating them to a point at which vulnerable plaques, which pose an ongoing risk factor for acute coronary syndrome (ACS) are stabilized; particularly to compositions containing statins, in combination with specific ratios of highly purified long chain fatty acid compositions which are effective in elevating omega-3 levels to a point at which the risk factors for cardiovascular disease are mitigated, and most particularly to a composition having an EPA:DHA:DPA ratio and level of omega-3 purity which enable them to be effective in stabilizing vulnerable plaque while providing a sustained vasodilatory effect, defined as a vasodilatory effect lasting at least 6 hours.

BACKGROUND OF THE INVENTION

Cardiovascular disease (CVD) represents the primary cause of mortality for men and women in developed countries globally. These premature deaths come at great cost to both the individuals and their families, as well as representing a huge burden to the health care system of the country. The risk factors for coronary heart disease are well-recognized and include: higher than average serum cholesterol, elevated levels of LDL; a low level of HDL in proportion to the LDL level; higher than average serum triglycerides; higher levels of lipid oxidation products creating plaques and streaks which cause blockages of coronary arteries, and in the case of vulnerable plaques, represent a causative factor in promulgating ACS. An additional risk factor for coronary heart disease and stroke is high blood pressure. Reduction in these risk factors is effective to reduces the prevalence of coronary heart disease and its many costs.

In accordance with the findings of the U.S. 2005 Dietary Guidelines Advisory Committee, 70% of Americans are omega-3 fatty acid deficient. Further studies indicate that over 84% of CVD patients are deficient in omega-3 fatty acids, specifically Eicosapentaenoic acid (EPA), Docosahexaenoic acid (DHA) and Docosapentaenoic acid (DPA).

Cardiovascular disease (CVD) represents the primary cause of mortality for men and women in developed countries globally. These premature deaths come at great cost to both the individuals and their families, as well as representing a huge burden to the health care system of the country. The risk factors for cardiovascular disease are well-recognized and include: higher than average serum cholesterol, elevated levels of LDL; a low level of HDL in proportion to the LDL level; higher than average serum triglycerides; and higher levels of lipid oxidation products and inflammatory processes creating plaques and streaks which cause blockages of coronary arteries. An additional risk factor for cardiovascular disease and stroke is high blood pressure. Reduction in these risk factors is effective to reduce the prevalence of CVD and its many costs.

Although in some cases, genetic predisposition contributes to CVD incidence, poor diet and sedentary lifestyle are major factors that contribute to increased risk for the development, and progression of CVD. Because of this, clinical management of CVD often includes an attempt to modify a patient's lifestyle to increase exercise, and incorporate a balanced diet, rich in omega-3 fatty acids. Due to non-compliance, and often an inability of a patient to adhere to lifestyle modifications, optimal patient care is not achieved through these efforts alone, and other therapeutic interventions or strategies must be considered.

Treatment options may include lipid-regulating medications, such as statins, or fibrates that act to lower low density lipoprotein (LDL) cholesterol and concomitantly APO-B and/or triglycerides (TG), metabolic components that are thought to contribute to atherosclerotic plaque buildup, and increase the risk for heart attack or stroke. However, many of these treatment options come with unwanted side effects that could add additional health risks, or cause physical discomfort.

With regard to obstruction of vessels with plaque, it is observed that plaque deposits can be large or small. In the case of large plaques, they may act to obstruct the vessel, causing a gradual incremental reduction in the size of the arterial lumen. This ongoing process may be treatable with medication, or the use of stents or the like to reopen arterial flow. In the case of small, but vulnerable plaques, these unstable deposits have the ability to suddenly burst, resulting in a cascade effect, which may lead to formation of a thrombus which obliterates blood flow in a coronary or cerebral artery, creating a myocardial infarction or stroke.

Statins are cholesterol-lowering drugs, which work by blocking an enzyme the liver needs for cholesterol production. There are at least a half-dozen statins available on the market, from a number of different manufacturers. These statins vary somewhat in their potency and ability to lower LDL cholesterol.

In the field of CVD prevention, there is no single prior art composition which reduces the variety of risk factors associated with this pervasive disease and which has wide spread applicability to the population in developed countries.

In one aspect, the present invention provides a novel composition, which may be incorporated into an orally administered dietary regimen for the reduction of risk factors associated with CVD. The composition of the invention represents a unique combination of one or more statins with an omega 3 fatty acid formulation which have been shown to reduce risk factors associated with CVD, and in one aspect contribute to the stabilization of vulnerable plaque.

Omega-3 fatty acids are natural polyunsaturated fats found in sea foods like fish and which are presently also available as dietary supplements. They contain more than one double bond in the aliphatic chain. They are named according to the number (>1), position and configuration of double bounds. The three major types of omega-3 fatty acids are alpha-linolenic acid (ALA), eicosapentaenoic acid (EPA), and docosahexaenoic acid (DHA). These omega-3 polyunsaturated fatty acids have been shown to protect against several types of cardiovascular diseases such as myocardial infarction, arrhythmia, atherosclerosis, and hypertension (Abeywardena and Head, 2001; Kris-Etherton et al., 2003). It is widely accepted that (EPA) (C20:5n-3) and (DHA) (C22:6n-3) are the major biological active polyunsaturated fatty acids contributing to the prevention of a variety of cardiovascular disorders by improving endothelium-dependent vasodilatation and preventing activation of platelets. Fish oil, EPA and DHA have been shown to induce relaxation and inhibit contraction by mechanisms that are endothelium-dependent (Shimokawa et al., 1987; Yanagisawa and Lefer, 1987). High contents of omega-3 polyunsaturated fatty acids, especially EPA, inhibited platelet aggregation and increased bleeding time, presumably due to a reduced generation of thromboxane $A_2$. Previous studies have also shown that dietary supplementation with cod-liver oil purified omega-3 fatty acids potentiated endothelium-dependent relaxations in isolated porcine coronary arteries (Shimokawa et al., 1988).

If a combination therapy including a novel omega-3 formulation in combination with one or more statins, could be provided for enhancing the patient's lipid profile and mitigating the various risk factors for cardiovascular disease, particularly reduction of overall serum cholesterol levels, reductions in high blood pressure, increase in the HDL:LDL ratio, reduction of triglycerides and homocysteine levels, reduction in apolipoprotein-B levels, and prevention of lipid oxidation, formation of plaques, and stabilization of vulnerable plaques, a long felt need would be realized.

SUMMARY OF THE INVENTION

The prior art fails to disclose a pharmaceutical formulation as set forth in the instantly disclosed invention, containing the combination of a statin and an omega-3 composition containing about 90% or greater omega 3 fatty acids by weight having a combination of Eicosapentaenoic acid (EPA) and Docosahexaenoic acid (DHA) in a weight ratio of EPA:DHA of from 5.7 to 6.3, wherein the sum of the EPA, DHA and DPA is about 82% by weight of the total formulation and about 92% of the total omega 3 fatty acid content of the composition. EPA+DHA are about 80% of the total formulation and about 89% of the total omega 3 fatty acid content of the composition. In combination, each of these components, which independently reduce one or more of the risk factors for cardiovascular disease (CVD), work synergistically to reduce the risk of CVD more effectively than any of these components taken alone.

It is noteworthy that tailoring the ratios, content and purity of omega fatty acid formulations provides the skilled artisan with a significant set of specific parameters, whereby formulations having a desired utility or pharmacological action may be derived.

The present inventors have discovered that the ability of omega-3 fatty acid preparations to cause endothelium-dependent relaxations depends on their relative content of EPA and DHA, as well as the purity of the overall formulation and the presence of additional key omega-3 fatty acids, particularly DPA.

Indeed, formulations in accordance with the present invention having an EPA:DHA ratio of about 6:1 induced significantly greater relaxations than an EPA:DHA 1:1 preparation despite their similar content of omega-3 fatty acids. These findings also suggest that EPA is likely to be a more potent endothelium-dependent vasorelaxant agonist than DHA. The fact that the two major omega-3 fatty acids do not have similar biological activity to cause endothelium-dependent relaxation is important since the leading commercial omega-3 preparation (Lovaza®) has a ratio of EPA:DHA 1.2:1. Thus, the optimization of the ratio of EPA:DHA in omega-3 preparations may provide new products with an enhanced vascular protective potential.

The present invention provides a novel composition, which may be incorporated into an orally administered formulation for the reduction of risk factors associated with CVD, and, in an embodiment, represents a novel treatment modality for the stabilization of vulnerable plaque. A composition of the formulation of the invention may also be used orally to treat and/or prevent risk factors of CVD and stroke, including reduction of high blood pressure and improving overall lipid profiles, e.g. low density lipoprotein (LDL), high density lipoprotein (HDL) and triglycerides. While not wishing to be bound by any particular theory, the inventors believe that the compositions work by acting at different sites and aspects of cardiovascular disease. The compositions of the present invention are preferably presented for administration to humans and animals in unit dosage forms, such as tablets, capsules, pills, powders, granules, and oral solutions or suspensions and the like, containing suitable quantities of an active ingredient.

The present invention also provides methods of treatment, for example administering to a patient having an omega-3 fatty acid deficiency, that may be evidencing one or more risk factors for CVD, a therapeutically effective amount of a formulation in accordance with the invention to achieve a therapeutic level of omega-3; whereby mitigation of said one or more risk factors for CVD is achieved. In certain embodiments, the invention is also a method for stabilization of vulnerable plaque, and providing a sustained vasodilatory effect in a patient by administering a therapeutically effective amount of a formulation in accordance with the invention, whereby an indomethacin-independent sustained vasodilatory effect is achieved.

By providing a method of treatment for mediating omega-3 deficiencies, use of the instant invention to improve the health of the heart and to reduce risk factors associated with cardiovascular disease by delivering to an individual the composition of the invention is realized. Delivery of the composition of the invention, e.g., by oral administration, has been shown to be useful for preventing the oxidation of low density lipoprotein (LDL), increasing high density lipoprotein (HDL), and for reducing total cholesterol. Delivery of the composition of the invention is also useful for reducing triglycerides and reducing homocysteine.

Desirably, the compositions of the invention are formulated such that an effective amount is delivered by multiple tablets, gelcaps or the like (or other suitable formulation) a day. Suitably, these doses may be taken with meals, mixed into food, or taken on an empty stomach. Generally improvement is observed after two to eight weeks of daily use. Optionally, the compositions of the invention may be delivered daily in a suitable form (e.g., a chew or bar). Other suitable dosage regimens may be readily developed by one of skill in the art. Such dosage regimens are not a limitation of the invention. The compositions of the present invention, in addition to their use in treating CVD in humans, may also be useful in treating non-human animals, particularly mammals. For example, these dietary supplements may be useful for companion animals such as dogs and cats, for cattle, horses, and pigs, among other animals.

A primary objective of the instant invention is to teach a combined therapy comprising a statin and an omega-3 fatty acid formulation. The combined therapy may be supplied either as single dosage forms or in a combined dosage form. One or more statins (HMG-CoA inhibitors) which are useful in the treatment of patients with hypertriglyceridemia, hypercholesterolemia, mixed dyslipidemia, atherosclerotic disease, coronary heart disease (CHD) and cardiovascular disease (CVD), wherein exemplary, albeit non-limiting examples are cerivastatin, atorvastatin, simvastatin, pravastatin, fluvastatin, lovastatin, rosuvastatin, eptastatin, pitavastatin, velostatin, fluindostatin, dalvastain, or pharmaceutically acceptable salts thereof or a combination thereof, are provided along with mixtures of an omega-3 fatty acid formulation containing a minimum of 90% omega 3 fatty acids by weight including a combination of Eicosapentaenoic acid (EPA) and Docosahexaenoic acid (DHA) in a weight ratio of EPA:DHA of from 5.7 to 6.3, wherein the sum of the EPA, DHA and DPA are about 82% by weight of the total formulation and about 92% of the total omega 3 fatty acid content of the composition. EPA+DHA are about 80% of the total formulation and about 89% of the total omega 3 fatty acid content of the composition. The combination is effective for correcting omega-3 deficiencies in patients in need thereof, thereby providing a mechanism for stabilizing vulnerable plaques, and thereby reducing the incidence of ACS and stroke, and for concomitantly reducing the risk factors for cardiovascular disease.

The fatty acids of the present invention are understood to include biologically active glyceride forms, e.g. triglycerides, biologically active ester forms, e.g. ethyl ester forms, and biologically active phospholipid forms, their derivatives, conjugates, precursors, and pharmaceutically acceptable salts and mixtures thereof. It is understood that the combination of omega-3 formulation and statins may be provided as a single unit dosage form, or as separate and distinct unit dosage forms.

A further objective of the instant invention is to teach methods of administering such combinations, and unit dosages of such combinations for the treatment of hypertriglyceridemia, hypercholesterolemia, mixed dyslipidemia, atherosclerotic disease, and vascular disease in cardiovascular disease patients (CVD), wherein the levels of apolipoprotein-B (APO-B) are lowered.

It is a further objective of the instant invention to provide a method and system for its practice to mediate omega-3 deficiency in patients having a need therefore, while assisting such patients in improving their lipid profile by the co-administration of a statin and an omega 3 fish oil.

These and other advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof. All examples are illustrative and non-limiting in view of the disclosure.

DETAILED DESCRIPTION OF THE INVENTION

Figure 1:
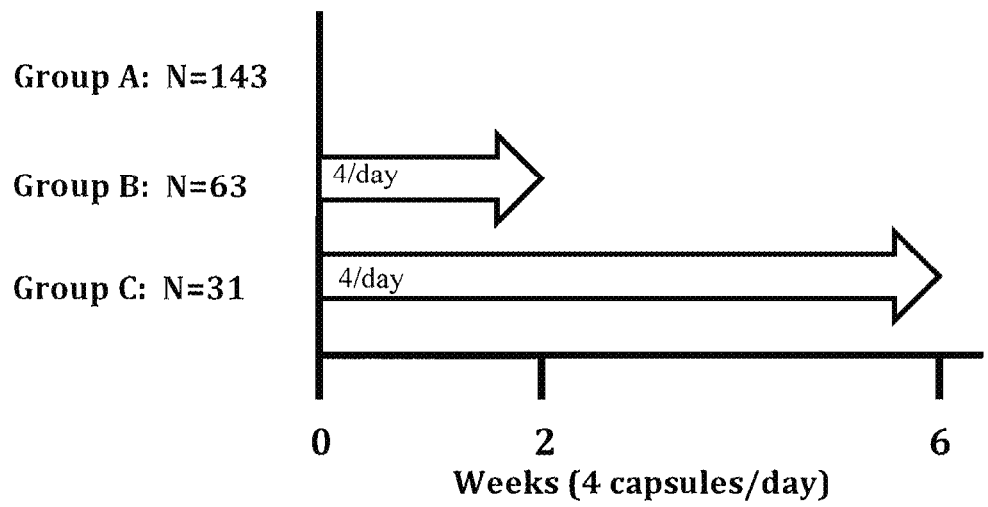
FIG. 1 illustrates the study design for the VASCAZEN™ open label study.

The present invention provides a combination therapy and a method for its use, which contains novel combinations of selected mixtures of one or more statins with an omega 3 fatty acid formulation.

The methods are useful in the treatment of patients with hypertriglyceridemia, hypercholesterolemia, mixed dyslipidemia, atherosclerotic disease, cardiovascular disease (CVD) and vascular disease.

The oral administration of these compositions acts to reduce serum cholesterol levels and blood pressure, increase HDL levels in proportion to LDL levels, thereby lowering APO-B levels, to protect lipids from oxidation thereby preventing the formation of plaques which block coronary arteries, and to lower both triglyceride levels and homocysteine levels. In addition, it is believed that oral administration of the compositions of this invention acts to reduce the risk of stroke, as well as heart attack, in human adults.

One particularly desirable embodiment of the invention is directed towards a composition and a method for its use including an HMG-CoA inhibitor, which is exemplified by, albeit not limited to cerivastatin, atorvastatin, simvastatin, pravastatin, fluvastatin, lovastatin, rosuvastatin, eptastatin, pitavastatin, velostatin, fluindostatin, dalvastain, or pharmaceutically acceptable salts thereof or a combination thereof; and an omega-3 fatty acid formulation.

With respect to the omega-3 component of the combination therapy and method of its use, the present invention provides a long chain fatty acid composition that includes a formulation containing a minimum of about 90% omega 3 fatty acids by weight having a combination of Eicosapentaenoic acid (EPA) and Docosahexaenoic acid (DHA) in a weight ratio of EPA:DHA of from 5.7 to 6.3, wherein the sum of the EPA, DHA and DPA is about 82% by weight of the total formulation and about 92% of the total omega 3 fatty acid content of the composition. EPA+DHA are about 80% of the total formulation and about 89% of the total omega 3 fatty acid content of the composition. The fatty acids of the present invention are understood to include biologically active glyceride forms, e.g. triglycerides, biologically active ester forms, e.g. ethyl ester forms, and biologically active phospholipid forms, their derivatives, conjugates, precursors, and pharmaceutically acceptable salts and mixtures thereof.

The pharmaceutical formulation of the instant invention is contemplated as being administered in amounts providing a daily dosage of 1 to 4 gm of said formulation. The pharmaceutical formulation at such dosage level being effective for stabilization of vulnerable plaques, the treatment or prophylaxis of risk factors of cardiovascular disease and the protection against sudden death in patients with CVD.

Pharmaceutical formulations of the instant invention may be provided wherein a unit form is a gel or liquid capsule.

An exemplary unit dosage form includes from about 645 to about 715 mg/gm EPA, for example about 680 mg/gm EPA and from about 105 to 115 mg/gm, for example about 110 mg/gm DHA. The unit dosage can include from about 22 to about 28 mg/gm DPA for example about 25 mg/gm DPA. Unit doses may additionally include a stabilizer, e.g. tocopherol in amounts up to about 0.5%, for example about 0.15% to about 0.25% or about 0.2% by weight. The effective unit dosage is generally 3 gm to 4 gm of the pharmaceutical formulation which are provided daily to CVD patients in one or more unit doses, for example about 3-4 one gram capsules per day. As set forth below, one or more optional ingredients can be included in the formulations. Such ingredients may be separately added or may be components of the source from which the omega 3 fatty acids in the formulation are derived.

In some embodiments, the formulation may further contain about 30 mg/gm of arachidonic acid (AA). In some embodiments, the formulation may further contain up to about 5%, for example about 3% or about 30 mg/gm of arachidonic acid (AA). It has been discovered that aspirin-acetylated COX-2 is also able to convert Omega-6 AA through lipoxygenases (LOX) to lipoxins (LXs), which are potent anti-inflammatory mediators (Nature Chemical Biology, Vol. 6, June 2010, Pp 401-402).

Some embodiments of the formulation contains >2%, for example >3%, of 18 carbon Omega-3 fatty acids, either individually or in total. Exemplary 18 carbon atom omega-3 include alpha-linolenic acid (ALA) and Stearidonic acid (SDA), either alone or in combination. Studies have shown that the presence of 18 carbon Omega-3s, such as ALA elicit anti-inflammatory effects (Zhao et al, Am J Clin Nutr 2007; 85:385-91). The composition is formulated with a specific amount of DHA consisting of about 400 mg per daily dose.

The composition can contain additional fatty acids in lesser amounts, usually less than about 1% of each that is present. Exemplary embodiments contain about 0.3-0.7%, or about 5% of any of the additional fatty acids. These additional fatty acids can include, for example, omega-6 fatty acids such as Dihomo-gamma-linolenic acid (DGLA; 20:3n6), Docosapentaenoic acid (Osbond acid; 22:5n6); omega-9 fatty acids such as Oleic acid (18:1n9) and others such as 7,10,13,15-hexadecatetraenoic acid and (16:4n1), 9,12,15,17-octadecatetraenoic acid (18:4n1). Other fatty acids may be present in higher quantities. For example, Eicosatetraenoic acid (ETA; 20:4n3) may be present in amounts up to about 2%, for example about 1.5%, and Heneicosapentaenoic acid (HPA; 21:5n3) may be present in amounts up to about 3%, for example at about 2.3%. These additional fatty acids may be added separately or may be present in formulations obtained from particular sources using particular methods. Other additional components and fatty acids may also be present in small amounts, for example 0-0.25% of the formulation.

The composition is formulated with a DHA content to provide about 400 mg per daily dose.

Daily administration of the formulation can reduce the level of triglycerides (TG) and increases high density phospholipids (HDL) levels, while lowering low density lipoprotein (LDL) levels in CVD patients.

A highly potent omega-3 formulation in accordance with the present invention is marketed by Pivotal Therapeutics, Inc., under the trade name VASCAZEN™, to alleviate the cardiovascular risks associated with omega-3 deficiency. VASCAZEN™, has been formulated for the dietary management of omega-3 deficiency in patients with CVD, providing EPA and DHA to levels not attainable through normal dietary modifications. More specifically, the VASCAZEN™ product exemplifies the present invention in being composed of about 90% or more omega-3 fatty acids at a ratio of eicosapentaenoic acid (EPA) to docosahexaenoic acid (DHA) within the range of 5.7:1-6.3:1, respectively. The formulation contains about 680 mg/g of EPA, about 110 mg/g of DHA, and about 25 mg/g of DPA per capsule. Each capsule has a total weight of about 1000 mg. It is generally contemplated that a daily regimen of VASCAZEN™ includes 4 tablets per day given either in one dose or in separate doses throughout the day. With respect to a 1000 mg fill, the formulation contains at least about 90% or more omega-3 fatty acids, wherein about 80% is the sum of EPA+DHA, and about 82% the sum of EPA+DPA+DHA. Embodiments can also contain about 30 mg/g of arachidonic acid, an omega-6 fatty acid, and/or >3% of 18 carbon Omega-3 fatty acids.

The present invention provides a novel composition, which may be incorporated into an orally administered formulation for the reduction of risk factors associated with CVD, and a novel treatment method. A composition of the formulation of the invention may be used orally to treat and/or prevent risk factors of CVD and stroke, including reduction of high blood pressure and improving overall lipid profiles, e.g. low density lipoprotein (LDL), high density lipoprotein (HDL) and triglycerides. While not wishing to be bound by any particular theory, the inventors believe that the compositions work by acting at different sites and aspects of cardiovascular disease. The compositions of the present invention are preferably presented for administration to humans and animals in unit dosage forms, such as tablets, capsules, pills, powders, granules, and oral solutions or suspensions and the like, containing suitable quantities of an active ingredient.

Pharmaceutical formulations of the instant invention may be provided wherein a unit form is a gel or liquid capsule.

An exemplary unit dosage form includes from about 645 to about 715 mg/gm EPA, for example about 680 mg/gm EPA and from about 105 to 115 mg/gm, for example about 110 mg/gm DHA. The unit dosage can include from about 22 to about 28 mg/gm DPA for example about 25 mg/gm DPA. Unit doses may additionally include a stabilizer, e.g. tocopherol in amounts up to about 0.5%, for example about 0.15% to about 0.25% or about 0.2% by weight. The effective unit dosage is generally 3 gm to 4 gm of the pharmaceutical formulation which are provided daily to CVD patients in one or more unit doses, for example about 3-4 one gram capsules per day. As set forth below, one or more optional ingredients can be included in the formulations. Such ingredients may be separately added or may be components of the source from which the omega 3 fatty acids in the formulation are derived.

In some embodiments, the formulation may further contain about 30 mg/gm of arachidonic acid (AA). In some embodiments, the formulation may further contain up to about 5%, for example about 3% or about 30 mg/gm of arachidonic acid (AA). It has been discovered that aspirin-acetylated COX-2 is also able to convert Omega-6 AA through lipoxygenases (LOX) to lipoxins (LXs), which are potent anti-inflammatory mediators (Nature Chemical Biology, Vol. 6, June 2010, Pp 401-402).

Some embodiments of the formulation contain >2%, for example >3%, of 18 carbon Omega-3 fatty acids, either individually or in total. Exemplary 18 carbon atom omega-3 include alpha-linolenic acid (ALA) and Stearidonic acid (SDA), either alone or in combination. Studies have shown that the presence of 18 carbon Omega-3s, such as ALA elicit anti-inflammatory effects (Zhao et al, Am J Clin Nutr 2007; 85:385-91).

The composition can contain additional fatty acids in lesser amounts, usually less than about 1% of each that is present. Exemplary embodiments contain about 0.3-0.7%, or about 5% of any of the additional fatty acids, These additional fatty acids can include, for example, omega-6 fatty acids such as Dihomo-gamma-linolenic acid (DGLA; 20:3n6), Docosapentaenoic acid (Osbond acid; 22:5n6); omega-9 fatty acids such as Oleic acid (18:1n9) and others such as 7,10,13,15-hexadecatetraenoic acid and (16:4n1), 9,12,15,17-octadecatetraenoic acid (18:4n1). Other fatty acids may be present in higher quantities. For example, Eicosatetraenoic acid (ETA; 20:4n3) may be present in amounts up to about 2%, for example about 1.5%, and Heneicosapentaenoic acid (HPA; 21:5n3) may be present in amounts up to about 3%, for example at about 2.3%. These additional fatty acids may be added separately or may be present in formulations obtained from particular sources using particular methods. Other additional components and fatty acids may also be present in small amounts, for example 0-0.25% of the formulation.

The composition is formulated with a DHA content to provide about 400 mg per daily dose.

Daily administration of the formulation can reduce the level of triglycerides (TG) and increases high density phospholipids (HDL) levels in CVD patients. Apolipoprotein-B levels are also lowered.

The daily dose of formulated composition provides a strong anti-inflammatory and mood enhancing effect with a specific amount of DHA for the protection against sudden death in patients with CVD.

According to a US study, and the Dietary Guidelines Committee, 70% of Americans are omega-3 deficient due to lack of consumption of this essential nutrient in the typical "western diet", which includes an overabundance of pro-inflammatory omega-6 fatty acid intake, by comparison. In patients with CVD, this dietary trend can be particularly dangerous. Coupled with other cardiometabolic risk factors, omega-3 deficiency further exacerbates the chronic progression of this disease. A growing body of evidence has demonstrated the cardiovascular health risks associated with chronic omega-3 deficiency. A dietary deficiency of EPA acid and DHA in particular, allows for downward pro-inflammatory pressures created by the metabolism of arachidonic acid (AA) that is typically very high in the diets of most Americans. Overall, omega-3 fatty acid deficiency contributes to a pro-inflammatory state, the consequences of which include negative effects on cardiovascular health, including increased risk for development of dyslipidemia (high cholesterol, high triglycerides), atherosclerotic plaque buildup, as well as the formation of unstable vulnerable plaque deposits, hypertension, and cardiac arrhythmia.

Chronic omega-3 deficiency can subsequently lead to increased risk for suffering a fatal heart attack, when unstable plaques suddenly burst, causing formation of a thrombus. Maintenance of blood levels of EPA, DHA and DPA above 6.1% of total blood fatty acids, compared to levels between 2.1%-4.3% is associated with an 80.0% lower risk of sudden cardiac death. To counterbalance the cardiovascular risks associated with an overabundance of AA, and the pro-inflammatory influences upon this metabolic pathway, one would need to increase EPA and DHA consumption to levels that can not be attained through dietary changes alone. Filling the "omega-3 nutritional void" thus requires additional supplementation with a highly potent EPA and DHA formulation, which provides high levels of EPA, as well as DHA, for full clinical benefit, removing a key risk factor in patients with CVD.

EXAMPLE

Subject#035-MH was a 55 year old male caucasian subject enrolled in the open label study of VASCAZEN, as described, and presented to the clinic with a medical history of cardiovascular disease. The patient was being treated by his cardiologist for hypertension and dyslipidemia for three years with the following medications: Crestor 200 mg (dyslipidemia, statin), Acebutolol 200 mg (hypertension, ACE inhibitor), Amlodipine 10 mg (hypertension), Irbesartan 300 mg (hypertension). Despite these interventions, the patient's lipid profile continued to pose significant cardiovascular health risks.

The patient was familiar with, and had tried over the counter omega-3 fish oil products, but without gaining any measurable clinical benefit, likely due to the low Omega-3 content of the products that were available to him Upon entering the trial, and providing informed consent, the subject was treated with VASCAZEN™ at a dose of 4 capsules per day, providing 2720 mg EPA, 440 mg DHA, and 100 mg DPA per day. After two months of treatment, the subject followed up with his own family practitioner, to obtain bloodwork (lipid panel for cholesterol and triglycerides), with the following results. His clinical improvement for dyslipidemia included a 58% reduction of triglycerides from 6.76 mmol/L to 2.84 mmol/L, a 26% reduction of LDL cholesterol from 3.15 mmol/L to 2.32 mmol/L with concomitant lowering of APO-B levels, an 8% reduction in total cholesterol from 5.19 mmol/L to 4.76 mmol/L, a 12% increase in HDL cholesterol from 1.03 mmol/L to 1.15 mmol/L, and a 17% reduction in the total cholesterol (TC)/HDL cholesterol ratio from 5.04 mmol/L to 4.14 mmol/L. No adverse events were reported with this individual.

In an open label study to analyze the safety and efficacy of VASCAZEN™, whole blood omega-3 fatty acid levels were examined in 143 patients, and the inventive formulation was administered to patients for two or six-week follow-ups, providing about 2800 mg/day EPA and about 480 mg/day DHA. The primary outcome measure was the change in the sum of blood EPA+DHA+DPA. levels (the Omega-Score™), expressed as a percentage of total blood fatty acid levels over a two or six-week duration.

The normalized baseline Omega-Score™ was 3.4% (N=143). In the two-week and six-week treated groups, the inventive formulation increased Omega-Score™ levels by 52.8% (N=63, p=<0.0001) and 120.6% (N=31, p=<0.0001) respectively, compared to baseline levels measured in each group. After six weeks of intervention, maximal, and stable levels were maintained at an average score of 7.5%. The formulation in accordance with the present invention was generally well tolerated, with only minor adverse events reported in a small proportion of study participants. (See Table 4)

Methodology:

The 6-week open label study was conducted at a single site in Canada. Subjects were eligible for the study if they met all inclusion and exclusion criteria set out in the clinical study protocol. All eligible subjects provided informed consent prior study enrollment, and entered Group A (FIG. 1.). Sixty three subjects were provided 4 capsules per day of VASCAZEN™ (Group B), an oral dose of 2720 mg EPA and 440 mg DHA per day. After two weeks of treatment, whole blood omega-3 blood level was assessed, and 31 subjects entered into Group C, for continued treatment. Group C subjects provided whole blood samples at weeks 4 and week 6, for follow-up Omega-Score™ assessment.

The primary outcome measure was the change in Omega-Score™ values expressed as a percentage of total blood fatty acid levels over a 2-week period for Group B, and 6-week period for Group C. The baseline Omega-Score' value for Group A was calculated as the mean percentage at week 0, prior to VASCAZEN™ intervention, and Groups B and C Omega-Score™ means were evaluated at the specified time points accordingly.

The study included both men and women >15 years of age, in stable medical condition. Exclusion criteria included the following: A history of ventricular arrhythmia, known bleeding or clotting disorder, liver or kidney disease, autoimmune disorder or suppressed immune systems, seizure disorder or taking anticonvulsant medication; allergies to fish; or subjects with an implantable cardioverter defibrillator. Medical histories, and current medications were also documented.

Laboratory analysis of total blood fatty acids in whole blood was conducted by a central laboratory, (University Health Network Laboratory, Toronto, Ontario), accredited by the College of American Pathologists' Laboratory Accreditation Program. Analysis was carried out by derivatizing fatty acids into methyl esters followed by Gas Chromatography-Mass Spectrometry (GC-MS) analysis (Agilent Technologies 6890N series gas chromatograph, 5975C detector, Mississauga, Ontario). Fatty acids were extracted from 200 μL of whole blood sample using a mixture of methanol and chloroform. Fatty acids were then methylated with 10% (w/v) $BCl_3$ in methanol by incubation at 90° C. for 25 min to form fatty acid methyl esters (FAMEs). After cooling the FAMEs were extracted with water/hexane mixture and 1 uL of n-hexane extract was injected for GC-MS analysis.

Sample size was justified accordingly. Assuming a mean baseline level of blood Omega-Score™ levels of at least 3.0% and a standard deviation in change of blood Omega-Score™ levels of 1.8% in the study population, the minimum sample size of 63 study subjects would result in a minimum power of 90.2% to detect an increase in blood Omega-Score™ levels following 2 weeks of study intervention of at least 25.0% relative to baseline, at a significance level of $\alpha=0.05$. The minimum sample size of 30 subjects taking VASCAZEN™ for six weeks would result in a minimum power of 94.2% to detect an increase in blood Omega-Score™ levels following 6 weeks of study intervention of at least 40.0% relative to baseline, at a significance level of $\alpha=0.05$. The safety population was defined as a patient group that had a minimum of 2 weeks and maximum of 6 weeks VASCAZEN™, at a dose of 4 capsules per day. Primary analyses of treatment efficacy was performed on the subset of enrolled study subjects for whom blood measurements were taken at baseline and after 2 weeks of study treatment. The change in blood Omega-Score™ levels over the 2-week period (expressed as a percentage change from baseline) was computed for each study subject. The distribution of changes in blood Omega-Score™ levels over 2 weeks were tested for normality using the Pearson-D'Agostino test. A paired t-test was conducted in order to test the change in blood Omega-Score™ levels over the 2-week period.

Secondary analyses of treatment efficacy was performed on the subset of enrolled study subjects for whom blood Omega-Score™ levels were taken at baseline and at time points of 2 weeks, 4 weeks and 6 weeks following baseline. An analysis of variance (ANOVA), utilizing subjects as blocks, was conducted to test the change in blood OmegaScore™ levels between any pair of time points over the 6-week period; multiple comparisons were conducted at a family-wide significance level of $\alpha=0.05$ in order to determine which pairs of time points (if any) differ significantly in terms of mean blood EPA+DHA+DPA levels. A linear contrast was carried out in order to test the hypothesis that mean blood EPA+DHA+DPA levels increase linearly within this subset of study subjects over the 6-week period.

Results:

Baseline characteristics of each study group are outlined in Table 1. Across all groups, age demographics were comparable, with the majority of study participants being middle-aged. Within group A, the mean age of the total group (N=143), consisting of mostly males (74.1%), was 50.9 years, and similar age distributions were observed between men (52.1), and women (46.9). Group B (N=63, 74.2% men), the two-week treatment group, had a mean age of 53.7, with comparable mean ages between men (55.8) and women (47.9). Finally, study subjects within group C (N=31, 87% men) had a mean age of 55.0 years (men, 54.0; women, 61.5). Baseline OmegaScore™ values were measured and all three groups, including men and women were found to have comparable, omega-3 deficient (defined as less than 6.1% Omega-Score)(N Engl J Med, Vol. 346, No. 15, Apr. 11, 2002, Pp. 1113-1118), scores between 3.3% and 3.8%.

TABLE 1

Baseline Characteristics*:

| | Group A | | |
|---|---|---|---|
| Characteristic | Men (N = 106) | Women (N = 37) | Total (N = 143) |
| Age, mean (SD) (years) | 52.1 ± 13.6 | 46.9 ± 15.0 | 50.9 ± 14.6 |
| *Omega-Score ™(%) | | | |
| Mean | 3.4 ± 1.4 | 3.5 ± 1.2 | 3.4 ± 1.3 |
| 95% CI | 3.2 to 3.7 | 3.2 to 3.7 | 3.2 to 3.6 |
| | (±1.1 to 1.6) | (±1.0 to 1.4) | (±1.1 to 1.6) |
| | Group B | | |
| Characteristic | Men (N = 47) | Women (N = 16) | Total (N = 63) |
| Age, mean (SD) (years) | 55.8 ± 10.9 | 47.9 ± 16.7 | 53.7 ± 13.1 |
| *Omega-Score ™(%) | | | |
| Mean | 3.8 ± 1.4 | 3.3 ± 1.3 | 3.6 ± 1.3 |
| 95% CI | 3.4 to 4.1 | 2.9 to 3.7 | 3.2 to 3.9 |
| | (±1.0 to 1.8) | (±0.9 to 1.7) | (±1.0 to 1.7) |

TABLE 1-continued

Baseline Characteristics*:

| | Group C | | |
|---|---|---|---|
| Characteristic | Men (N = 27) | Women (N = 4) | Total (N = 31) |
| Age, mean (SD) (years) | 54.0 ± 8.7 | 61.5 ± 11.0 | 55.0 ± 9.2 |
| *Omega-Score ™(%) | | | |
| Mean | 3.7 ± 1.2 | N/A | 3.4 ± 1.2 |
| 95% CI | 3.3 to 4.0 | N/A | 3.1 to 3.7 |
| | (±0.8 to 1.5) | | (±0.8 to 1.5) |

Omega-Score ™ calculated as the mean +/− SD (where N = number of subjects) from a normal distribution of raw data. Group C (women) did not have sufficient numbers to fit a normal distribution curve. The mean baseline score of the raw data for this group was 2.98%.

Figure 2:
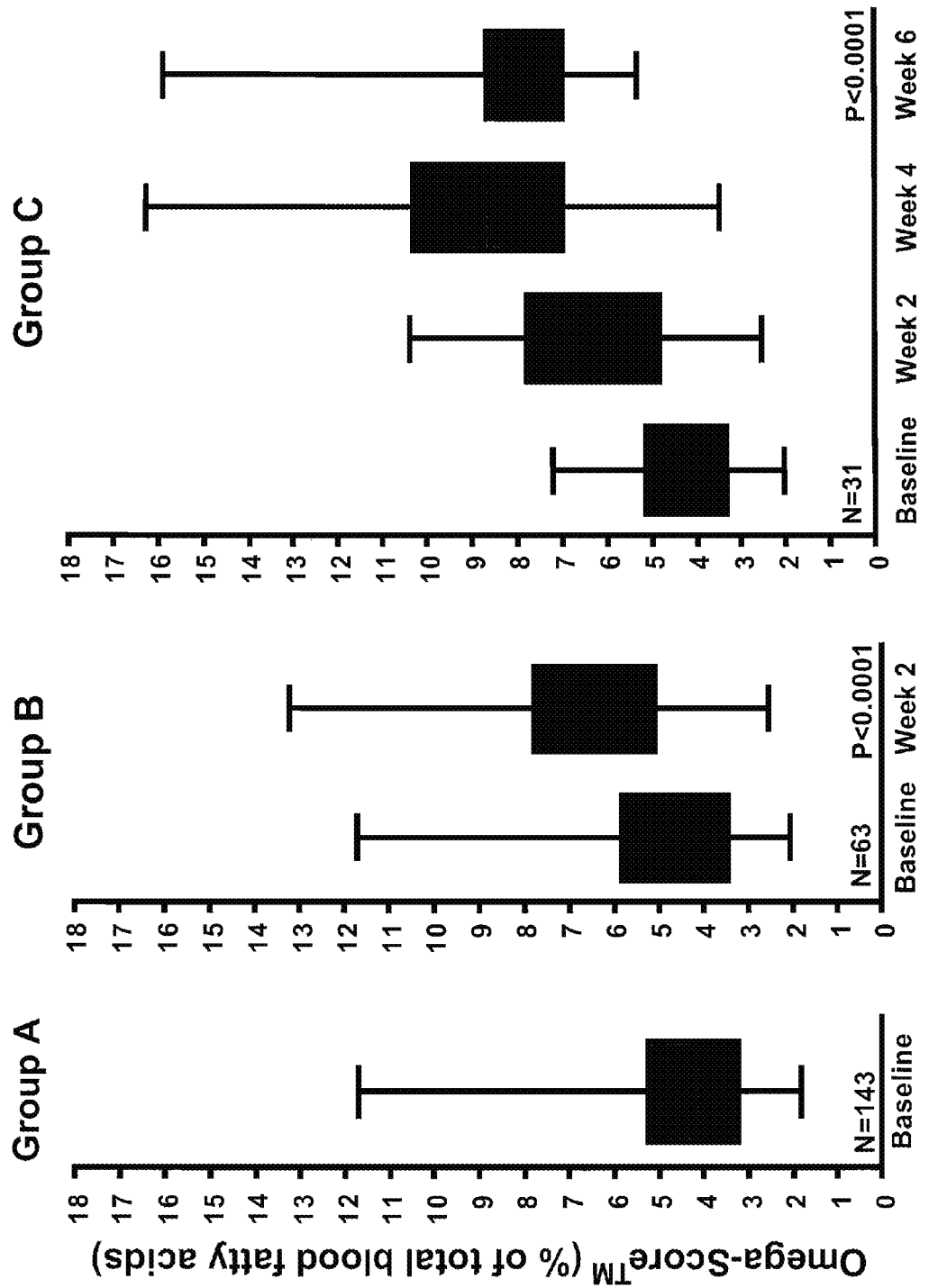
FIG. 2 is a plot of improved whole blood EPA+DHA+DPA levels baseline to week 6.
Figure 3:
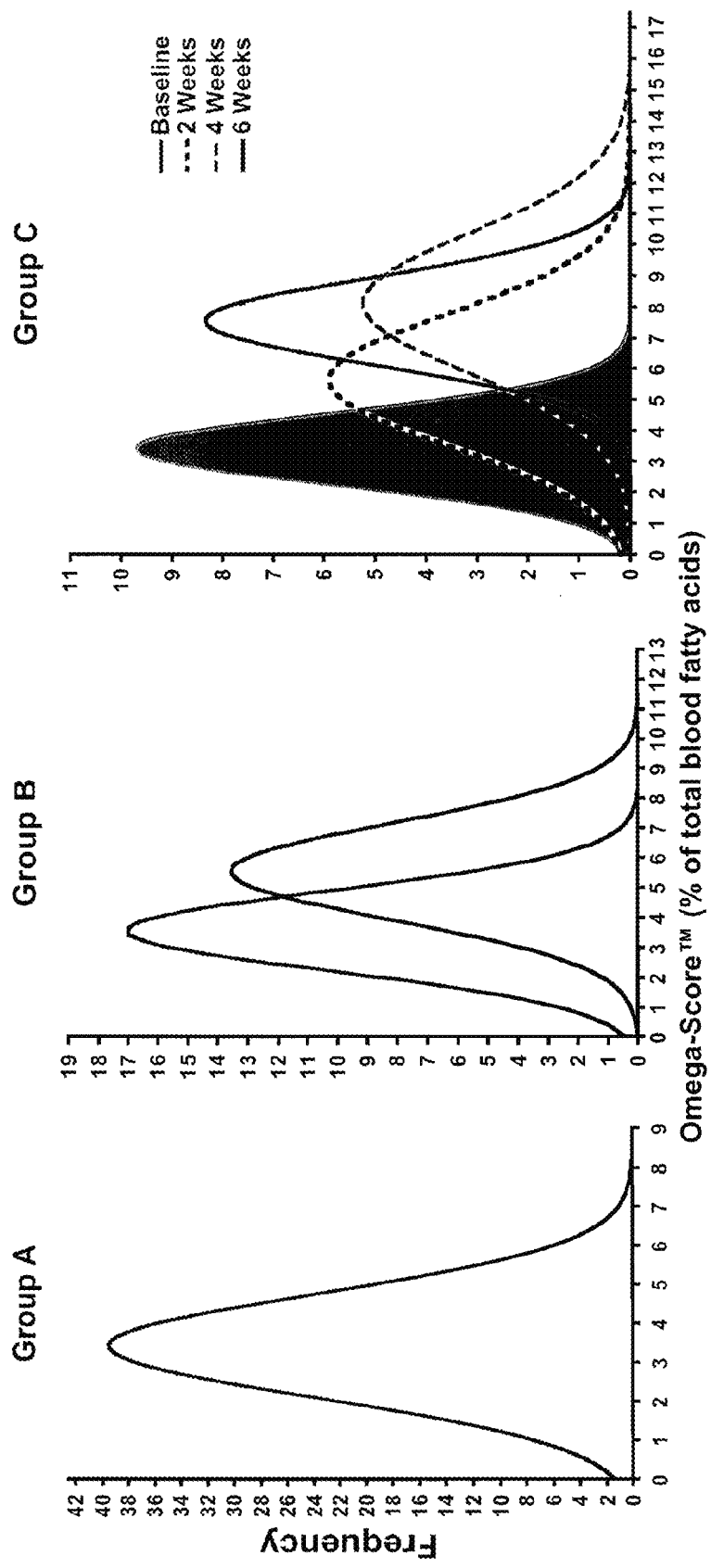
FIG. 3 illustrates the normal distribution curves for Groups A-C during the Open Label Study.

Results of the primary outcome measure are illustrated in FIG. 2 and Table 2, and calculated/fit to a normal distribution in FIG. 3, Table 3. Baseline levels of whole blood omega-3 blood levels revealed an omega-3 deficiency (group A) in a large study group (N=143). Within this group, subjects had a mean score of 4.4%, or 3.4% (normal distribution curve fit), representing 84.5% of individuals with scores below a 6.1% score cutoff, cardiovascular disease risk quartile. Study participants that received VASCAZEN™ intervention for 2 weeks (group B) had a significant (P<0.0001) improvement in their scores (FIG. 2, Table 2), with mean values improving from 3.6% to 5.5% (FIG. 3, Table 3), a 52.8% score increase. Over two weeks of intervention, study participants considered "at risk" were reduced from 80.6% to 46.8% (Table 3). Over the course of 6 weeks VASCAZEN™ intervention, group C subjects had significant mean score improvements (P<0.0001)(FIG. 2, Table 2), with mean values improving from 3.4% to 7.5% between baseline and week 6 (FIG. 3, Table 3), and representing a 120.6% increase in whole blood levels of EPA+DHA+DPA Omega-Score™ values. After 6 weeks of VASCAZEN™ intervention, 13.2% of participants remained at higher risk (<6.1% Omega-Score™), Table 3.

TABLE 2

Table 2. Primary Outcome Measure: Change in the sum of blood EPA + DHA + DPA levels expressed as a percentage of total blood fatty acid levels over a two or six-week intervention

| | Omega-Score ™ Mean ± SD (%) (% change from baseline) |
|---|---|
| Group A (N = 143) | |
| Baseline | 4.4 ± 1.7 |
| Group B (N = 63) | |
| Baseline | 4.7 ± 1.9 |
| Week 2 | 6.7 ± 1.9 (52.8%) |
| Group C (N = 31) | |
| Baseline | 4.3 ± 1.5 |
| Week 2 | 6.4 ± 2.1 (48.8%) |
| Week 4 | 8.6 ± 2.4 (100.0%) |
| Week 6 | 8.2 ± 2.0 (90.7%) |

TABLE 3

Table 3. Primary Outcome Measure: Change in the sum of blood EPA + DHA + DPA levels expressed as a percentage of total blood fatty acid levels over a two or six-week intervention, and represented as a normal distribution.

| | Omega-Score ™ (%) | | |
|---|---|---|---|
| | Mean ± SD (% change from baseline) | 95% CI | % of Patients At Risk (<6.1% Omega-Score ™) |
| Group A (N = 143) | | | |
| Baseline | 3.4 ± 1.3 | 3.1 to 3.7 (±0.9 to 1.4) | 84.5% |
| Group B (N = 63) | | | |
| Baseline | 3.6 ± 1.3 | 3.2 to 3.9 (±1.0 to 1.7) | 80.6% |
| Week 2 | 5.5 ± 1.6 (52.8%) | 5.1 to 6.0 (±1.2 to 2.1) | 46.8% (−33.8%) |
| Group C (N = 31) | | | |
| Baseline | 3.4 ± 1.3 | 3.1 to 3.7 (±0.9 to 1.4) | 84.5% |
| Week 2 | 5.7 ± 1.9 (67.6%) | 5.4 to 6.3 (±1.4 to 2.3) | 43.2% (−41.3%) |
| Week 4 | 7.9 ± 2.4 (132.4%) | 6.6 to 9.1 (±1.2 to 3.7) | 15.0% (−69.5%) |
| Week 6 | 7.5 ± 1.2 (120.6%) | 7.0 to 8.0 (±0.7 to 1.7) | 13.2% (−71.3%) |

Patients with >6.1% (ideal) scores had an 80% less chance of death from sudden cardiac arrest, compared to individuals in the 2.1%-4.3% risk quartile (score) range. In this study, the mean baseline value of the study population indicated that 84.5% of study participants, many of which with cardiovascular health issues, on statin, and/or blood pressure medication, had scores less than 6.1%, leaving themselves at greater risk for adverse events, especially in patients with known dyslipidemia, type 2 diabetes, and/or hypertension. After six weeks of VASCAZEN™ intervention, 71.3% of group C participants with previous baseline scores less than 6.1% were able to increase their score to a level above this threshold.

TABLE 4

| Adverse Event Description | 2-6 Weeks Treatment (N = 63) | Severity | Relationship to Study Treatment |
|---|---|---|---|
| Reflux/Aftertaste | 2 | Mild | Definite |
| Minor Leg Bruising | 1 | Mild | Unrelated* |

*Minor bruising appeared after two weeks of treatment and disappeared within 3 days. The subject continued taking VASCAZEN ™ for additional four week without any adverse event.

Group B study participant scores significantly increased (P<0.0001) by 52.8% from 3.6% to 5.5%. With prolonged VASCAZEN™ intervention, group C individuals had significant score improvement over the course of 6 weeks (P<0.0001, ANOVA), with similar improvements as the group B individuals within two weeks. After 4 weeks, VASCAZEN™ significantly (P<0.0001) increased mean scores from 3.4% to 7.9%, representing a 132.4% improvement, bringing the mean score of the total population to well within the >6.1% low risk quartile. Indeed, only 15% of study participants remained below this benchmark level after 4 weeks, a level that is sustained in the study group through 6 weeks of VASCAZEN™ intervention. VASCAZEN™ was generally well tolerated with a low incidence, of minor adverse events that are typical for omega-3 polyunsaturated fatty acid ethyl esters. This study has highlighted the prevalence of chronic omega-3 deficiency in the majority of people (84%), both men and women.

The consequences of omega-3 deficiency in patients with CVD are well documented, with numerous studies linking EPA and DHA deficiency. Many studies and current therapeutic approaches have categorized omega-3 as a therapeutic agent for the treatment of symptoms that accompany CVD. Unfortunately the common thread of thought around omega-3 fatty acid therapy does not lead to optimal results. EPA and DHA should not be considered therapeutic agents, rather, they should be considered essential nutrients, which should ideally be consumed regularly as part of a healthy balanced diet. Omega-3 deficiency in patients with CVD adds unnecessary risks, that can be avoided with suitable omega-3 supplementation. The present invention as exemplified by VASCAZEN™ intervention provides essential balanced levels of EPA and DHA that are difficult for many CVD patients to incorporate into their daily diet through food alone. In the typical western diet, the average American consumes 15 times less omega-3 fatty acids from fish than what is required to attain and maintain clinically beneficial levels of EPA and DHA. In order to consume enough of this essential nutrient to provide the daily dose that the present invention can provide, one would have to eat fish every single day, for more than one meal per day. This is unrealistic for most people.

The present study has demonstrated that maintenance of EPA+DHA+DPA to levels >6.1% can be achieved with the present invention within 4 weeks of intervention, and that over 85% of patients can achieve these levels at a dose of 4 capsules per day, supplying about 2720 mg EPA and 440 mg DHA. These findings support the use of omega-3 fatty acid supplements according to the present invention for the maintenance of routinely measured (via Omega-Score' assessment), clinically beneficial EPA+DHA+DPA blood levels in patients with CVD.

Sustained Vasodilatory Effect:

In addition to the benefits outlined above with respect to omega-3 supplementation for an omega-3 deficient patient population, formulations according to the invention have been shown to provide a sustainable eNOS vasodilatory effect, defined as a vasodilatory effect persisting for 6 hours or more, which has heretofore not been achievable with either prescription or OTC grade omega-3 supplements.

To understand this vasodilatory effect in the context of treatment and prevention of cardiovascular disease, it is first necessary to understand the mechanism of vasodilation via the endothelium lining of blood vessels.

The following list of Abbreviations will be relied upon for the following discussion.

Abbreviation List

Abbreviation Signification
[$Ca^{2+}$]i Intracellular free calcium concentration
APA Apamin
CaM Calmodulin
CaMK-2 Calmodulin kinase-2
cAMP Cyclic adenosine 3': 5' monophosphate
cGMP Cyclic guanosine 3': 5' monophosphate
EDHF Endothelium-derived hyperpolarizing factor
eNOS Endothelial NO synthase
ET-1 Endothelin-1
$H_2O_2$ Hydrogen peroxide
IKCa Calcium-dependent Intermediate conductance Potassium Channels
Indo Indomethacin
L-NA N-ω-nitro-L-arginine
MnTMPyP Mn (III) tetrakis (1-methyl-4-pyridyl) porphyrin
NO Nitric oxide
$O_2^{\circ}$— Superoxide anion
PEG-Catalase Polyethylene glycol-catalase
$PGI_2$ Prostacyclin I2
PI3-K Phosphoinositide-3 kinase
PKC Protein kinase C
PP2 4-amino-5-(4-chlorophenyl)-7-(t-butyl) pyrazolo[3,4]pyrimidine
ROS Reactive oxygen species (Reactive Oxygen Species)
sGC Soluble guanylyl cyclase
SKCa $Ca^{2+}$-dependent small conductance potassium channels
SOD Conductance Superoxide dismutase
TRAM34 1-[(2-Chlorophenyl)diphenylmethyl]-1H-pyrazole
$TX_{A2}$ Thromboxane A2
U46619 9,11-dideoxy-9-prostaglandin F2 methanoepoxy The endothelium consists of a single endothelial cell layer lining the luminal surface of all blood vessels. Endothelial cells play an important function in the regulation of vascular homeostasis. They regulate the contact of blood with the underlying thrombogenic arterial wall. They respond to numerous physiological stimuli such as circulating hormones and shear stress by releasing several short-lived potent endothelium-derived vasoactive factors such as nitric oxide (NO) and endothelium-derived hyperpolarizing factor (EDHF), these two factors playing a major role in the control of vascular tone (Busse et al., 2002; Michel and Feron, 1997). In addition, endothelial cells can also generate prostacyclin ($PGI_2$), a prostanoid causing relaxation of some blood vessels.

Endothelium-Derived Nitric Oxide (NO):

NO is produced by endothelial nitric oxide synthase (eNOS) from L-arginine, NO plays critical roles in normal vascular biology and pathophysiology. NO induces relaxation of the vascular smooth muscle by activating soluble guanylyl cyclase resulting in the formation of cyclic guanosine 3'-5'monophosphate (cGMP). In addition to the regulation of vascular tone and inhibition of platelet aggregation, NO also inhibits many key steps involved in atherogenesis including vascular smooth muscle cell proliferation, monocyte adhesion (Dimmeler et al., 1997; Hermann et al., 1997; Tsao et al., 1996) and cell death. eNOS can be activated by receptor-dependent and -independent agonists as a consequence of an increase in the intracelluar concentration of free Ca ([$Ca^{2+}$]i) and the association of a $Ca^{2+}$/calmodulin (CaM) complex with eNOS leading to its activation (Fleming et al., 2001). Indeed both the agonist-induced NO formation and subsequent vasorelaxation are abolished by the removal of $Ca^{2+}$ from the extracellular space as well as by CaM antagonists. eNOS is also regulated in endothelial cells at a post-translational level primarily through protein/protein interactions and multisite phosphorylation at Ser116, Thr497, Ser635, and Ser1179 (residue numbers are for the bovine sequence, equivalent to Ser114, Thr495, Ser633, and Ser1177 in the human sequence (Bauer et al., 2003; Boo et al., 2002; Dimmeler et al., 1997). Indeed, eNOS has been shown to be regulated by the interaction with positive and negative protein modulators such as caveolin (Cav-1) and heat shock protein 90 (Garcia-Cardena et al., 1998; Ju et al., 1997; Pritchard et al., 2001). In the basal state, the majority of eNOS appears to be bound to caveolin-1 with its enzymatic activity being repressed in the caveolae (Michel et al., 1997). This tonic inhibition of eNOS can be released by displacing caveolin-1 with $Ca^{2+}$/CaM in response to $Ca^{2+}$ mobilizing agonists (Ju et al., 1997). In addition to these modulators, phosphorylation of eNOS at key regulatory sites plays an important a role in the regulation of enzyme activity in response to several physiological stimuli (Ju et al., 1997). It has been shown that phosphorylation of eNOS at Ser1179 is associated with increased enzyme activity (Gallis et al., 1999; McCabe et al., 2000). Phosphorylation of eNOS-Ser1179 is regulated by PI3-kinase-dependent mechanisms (Gallis et al., 1999). Akt, one of the major regulatory targets of PI3-kinase, has been shown to directly phosphorylate eNOS at Ser1179 and activate the enzyme in response to vascular endothelial growth factor (VEGF), sphingosine-1-phosphate, and estrogens (Dimmeler et al., 1997; Fulton et al., 1999). However, eNOS-Ser1179 can also be phosphorylated by AMP-activated protein kinase (Busse et al., 2002), protein kinase A (PKA), and protein kinase G (PKG). Exactly which protein kinase(s) phosphorylates eNOS-Ser1179 in intact cells appears to be dependent on the type of endothelial cells and stimuli. For example, shear stress phosphorylates eNOS Ser1179 by a PI3-kinase- and PKA-dependent manner without involving Akt whereas EGF phosphorylates eNOS Ser1179 by a PI3-kinase- and Akt-dependent manner (Boo et al., 2002). In addition, the ischemia-reperfusion injury activates the PKA pathway leading to the phosphorylation of eNOS at Ser1179 and Ser635 (Li et al., 2010). In addition, the level of eNOS expression can be modulated by several factors including shear stress (Butt et al., 2000), hypoxia, low-density lipoproteins (LDL) (Chen et al., 2008; Chen et al., 1999) and oxidized fatty acids (Corson et al., 1996).

Endothelium-Derived Hyperpolarizing Factor (EDHF):

Endothelium-dependent vasorelaxation has also been observed in some blood vessels following inhibition of NO and PGI2 synthesis and has been attributed to endothelium-derived hyperpolarizing factor (EDHF). EDHF relaxes blood vessels through hyperpolarization of the vascular smooth muscle. This effect will close voltage-operated $Ca^{2+}$ channels resulting in reduction of the intracellular free $Ca^{2+}$ level and subsequent relaxation of the vascular smooth muscle. Potassium ($K^+$) channels underlie the hyperpolarization induced by EDHF and involve intermediate conductance $Ca^{2+}$-activated $K^+$ (IKCa) channels and small conductance $Ca^{2+}$-activated $K^+$ (SKCa channels). In several disease conditions including the presence of cardiovascular risk factors, the endothelium undergoes functional and structural alterations and it loses its protective role, and becomes proatherosclerotic (Vanhoutte, 1989). The loss of the normal endothelial function is referred to as endothelial dysfunction, which is characterized by impaired NO bioavailability subsequent to a reduced generation of NO by eNOS and/or an increased breakdown of NO by reactive oxygen species (ROS) and, in particular, superoxide anions (Vanhoutte, 1989).

Previous studies by the present inventors have indicated that natural products such as Concord grape juice (Anselm et al., 2007) and red wine polyphenols (Ndiaye et al., 2005) activate the endothelial formation of NO by causing the redox-sensitiveSer/PI3-kinase/Akt pathway-dependent phosphorylation of eNOSat Ser1177.

Fish oil omega-3 is a rich source of EPA and DHA. Omega-3 fatty acids have been shown to cause endothelium-dependent vasorelaxation in vitro in rat aortic rings and coronary artery rings by stimulating the endothelial formation of NO (Engler et al., 2000; Omura et al., 2001). However, the signal transduction pathway leading to eNOS activation remains poorly studied. Moreover, little information is currently available regarding the optimal ratio of EPA:DHA for the activation of eNOS. Therefore, the following experiments were carried out to characterize the fish oil-induced activation of eNOS in isolated blood vessels and cultured endothelial cells.

The initial experiment was designed to determine the ability of omega-3 fatty acids (EPA, DHA and different ratios of EPA:DHA) to cause endothelium-dependent relaxations in rings of porcine coronary arteries, thereby enabling the characterization of the role of NO and EDHF in endothelium-dependent relaxation and identification of the signal transduction pathway involved.

Additional experiments were designed to determine the ability of omega-3 fatty acids (EPA, DHA and different ratios of EPA:DHA) to cause activation of eNOS in cultured endothelial cells and to determine the underlying signal transduction pathway.

In order to make the above determinations we designed an experiment to codify vascular reactivity. Initially, the left circumflex coronary artery harvested from fresh pig hearts is cleaned of its fat and adherent tissue and cut into rings 2 to 3 mm in length. Rings without endothelium were obtained mechanically by rubbing with a pair of pliers inserted into the vessel lumen. Rings with or without endothelium were suspended in organ baths containing Krebs bicarbonate solution (composition in mM: NaCl 118.0, KCl 4.7, $CaCl_2$ 2.5, $MgSO_4$ 1.2, $NaHCO_3$ 23.0; $KH_2PO_4$ 1.2 and glucose 11.0, pH 7.4, 37° C.) oxygenated with a mixture of 95% 02 and 5% $CO_2$. After equilibrating rings for 90 min at a basal tension of 5 g, rings were contracted with KCl (80 mM) to verify the responsiveness of the vascular smooth muscle. After a 30 min washing period, the integrity of the endothelium was verified. Rings were contracted with U46619 (1-60 nM, an analogue of thromboxane A2) to 80% of the maximal contraction, and at the plateau of the contraction, bradykinin (0.3 µM) was added to check the presence of a functional endothelium. After repeated washings and return to baseline, rings were contracted again with U46619 before applying an increasing range of omega-3 fatty acids (0.001% to 0.4% v/v) to test their ability to induce relaxation of coronary artery rings. During the stabilization phase (30 min before contraction with U46619) different pharmacological tools were added to the Krebs bicarbonate solution to characterize the signaling pathway leading to endothelium-dependent relaxations:

a. Indomethacin (10 µM), an inhibitor of cyclooxygenases (COX) to prevent the formation of vasoactive prostanoids, particularly prostacyclin, b. Nω-nitro-L-arginine (L-NA, 300 µM), a competitive inhibitor of NO synthase (NOS) to overcome the NO component, and c. TRAM 34 (100 nM) and apamin (100 nM) inhibitors of $Ca^{2+}$-activated potassium channels (IKCa and SKCa) respectively, to overcome the EDHF component.

Pig coronary artery endothelial cells were harvested, cleaned with phosphate buffered saline solution (PBS) without calcium to remove any residual blood. Endothelial cells were isolated by collagenase (type I, Worthington, 1 mg/ml, 14 min at 37° C.) and cultured in medium MCDB 131 (Invitrogen) supplemented with 15% v/v fetal calf serum, 2 min glutamine, 100 U/mL penicillin, 100 U/mL streptomycin and 250 mg/ml fungizone (Sigma, St Louis, Mo.) at 37° C. in 5% $CO_2$. All experiments were performed with confluent endothelial cells used at first passage. Endothelial cells were exposed to MCDB131 with 0.1% v/v fetal calf serum 5 h before treatment with different substances.

After treatment, endothelial cells were rinsed twice with PBS and lysed with extraction buffer (composition in mM:

Tris/HCl 20, pH 7.5 (QBiogene), NaCl 150, Na$_3$VO$_4$ 1, Na$_4$P$_2$O$_7$ 10, NaF 20, okadaic acid 0.01 (Sigma), protease inhibitors (Complete Roche) and 1% Triton X-100). 25 µg of total proteins were separated on SDS-polyacrylamide (Sigma 8%) at 100 V for 2 h. Separated proteins were transferred onto a polyvinylidene fluoride membrane (Amersham) by electrophoresis at 100 V for 2 h. The membranes were blocked with blocking buffer containing 3% bovine serum albumin in TBS-T (Tris-buffered saline solution, Biorad, containing 0.1% Tween 20, Sigma) for 1 h. For detection of proteins, membranes were incubated in TBS-T containing the respective primary antibodies (p-eNOS Ser 1177, p-eNOS Thr 495 and p-Akt Ser 473 (dilution 1:1000), β-tubulin (dilution 1:5000, Cell Signaling Technology) overnight at 4° C. After a washout period, the membranes were incubated with secondary antibodies (anti-rabbit for p-eNOS, p-Akt, and anti-mouse for (3 tubulin) coupled to horseradish peroxidase (Cell Signaling Technology, dilution 1:5000) at room temperature for 1 h. Stained protein markers (Invitrogen) were used for the determination of the molecular weight of separated proteins. Immunoreactive bands were detected using chemiluminescence (Amersham).

All results were presented as mean±standard error of mean (SEM). n indicates the number of different coronary arteries studied. Statistical analysis was performed using Student t test or analysis of variance (ANOVA) test followed by Bonferoni post-hoc test. A P value of <0.05 is considered statistically significant.

Figure 4:
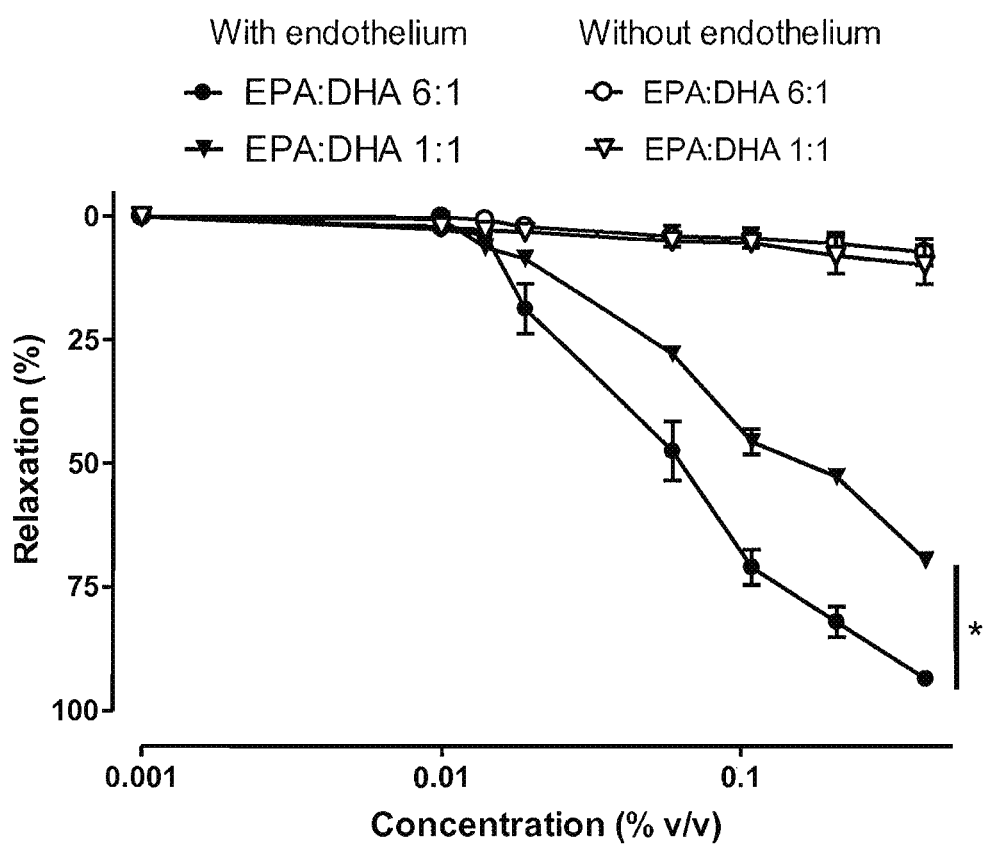
FIG. 4 illustrates the effect of differing EPA:DHA ratios on the relaxation of coronary artery rings with and without the presence of the endothelium.

Results:

The omega-3 fatty acid preparation EPA:DHA 1:1 induced concentration-dependent relaxations of coronary artery rings with endothelium whereas only small relaxations were obtained in those without endothelium contracted with U46619 (FIG. 4). The relaxations to EPA:DHA 1:1 was observed at volumes greater than 0.01% v/v and they reached about 75% at 0.4% v/v (FIG. 4). In addition, the omega-3 fatty acid preparation EPA:DHA 6:1 also induced endothelium-dependent relaxations which were more potent than those induced by EPA:DHA 1:1 (FIG. 4). Relaxations to EPA:DHA 6:1 started at 0.01% v/v and they reached about 98% at 0.4% v/v (FIG. 4). These findings indicate that the omega-3 fatty acid preparation EPA:DHA 6:1 is more effective to induce endothelium-dependent relaxations of coronary artery rings than the EPA:DHA 1:1 preparation. Thereafter, all subsequent experiments were performed with the omega-3 fatty acid preparation EPA:DHA 6:1.

It was determined that the omega-3 fatty acid preparation EPA:DHA 6:1 induces endothelium-dependent relaxations involving both NO and EDHF.

Figure 5:
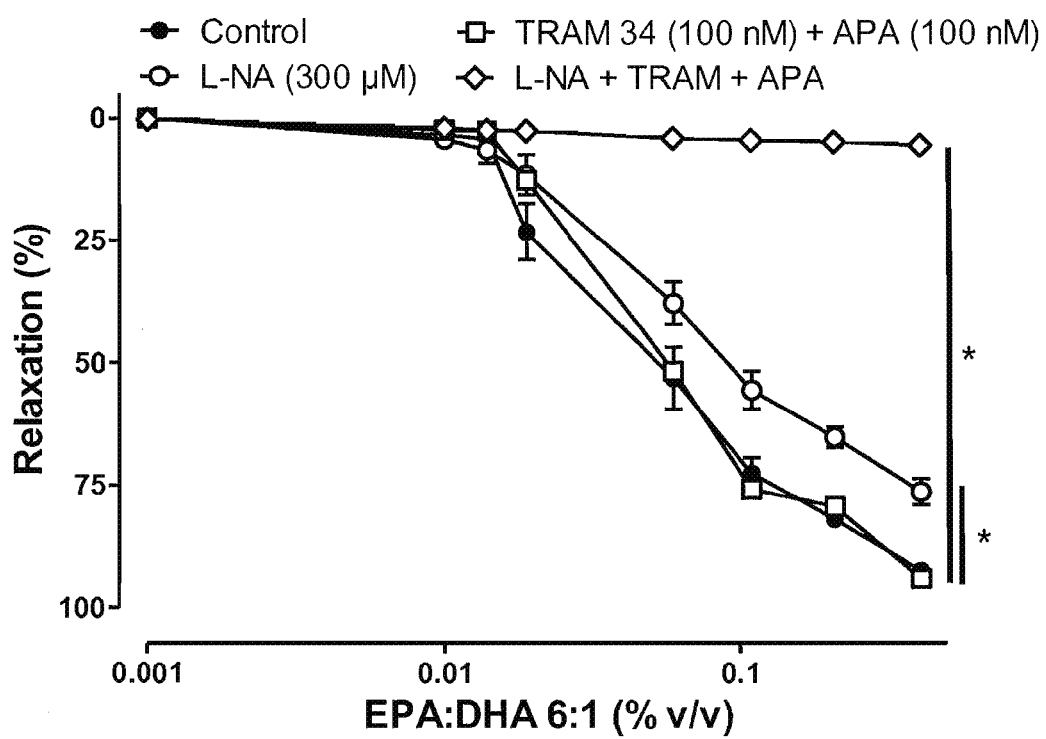
FIG. 5 discloses the relaxation effect of an EPA:DHA 6:1 control versus the effect of eNOS and EDHF inhibitors.

Previous studies have indicated that EPA and DHA induce relaxation of coronary artery rings by a mechanism mainly endothelium-dependent and sensitive to inhibitors of the formation of NO and EDHF (Omura et al., 2001). Therefore, a study to determine whether the endothelium-dependent relaxations induced by omega-3 fatty acid formulations having an EPA:DHA ratio of about 6:1 according to the present invention (referred to as EpA:DHA 6:1 herein) involve NO and EDHF was undertaken. The endothelium-dependent relaxation to EPA:DHA 6:1 was not significantly affected by inhibitors of the EDHF component, TRAM 34 and apamin (inhibitors of Ca$^{2+}$-dependent potassium channels of intermediate and low conductance IKCa and SKCa, respectively, FIG. 5). In contrast, relaxations were partially inhibited, but in a statistically significant amount, by L-NA (a competitive inhibitor of eNOS), indicating the involvement of NO (FIG. 5). In addition, the combination of L-NA plus TRAM 34 and apamin abolished the endothelium-dependent relaxation to EPA:DHA 6:1 (FIG. 5). Altogether, these findings indicate that EPA:DHA 6:1 induces endothelium-dependent relaxations which are mediated predominantly by NO and also, to a lesser extent, by EDHF.

Figure 6:
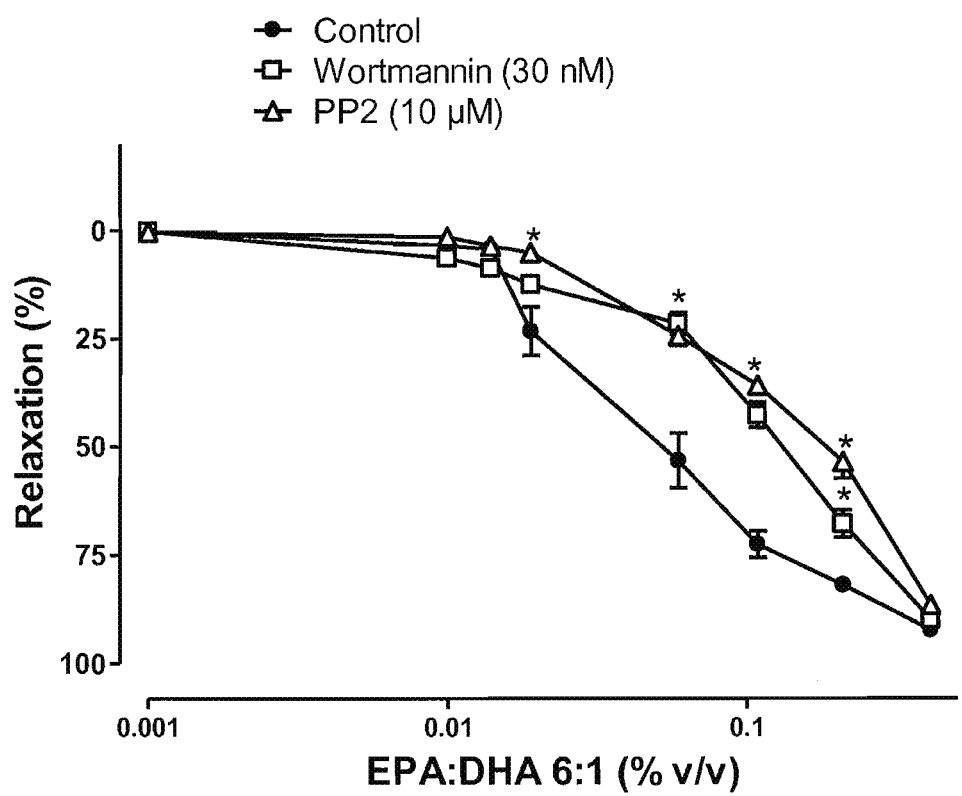
FIG. 6 discloses how the presence of Src kinase and PI3-kinase impacts the relaxation effect of an EPA:DHA 6:1 product.
Figure 7:
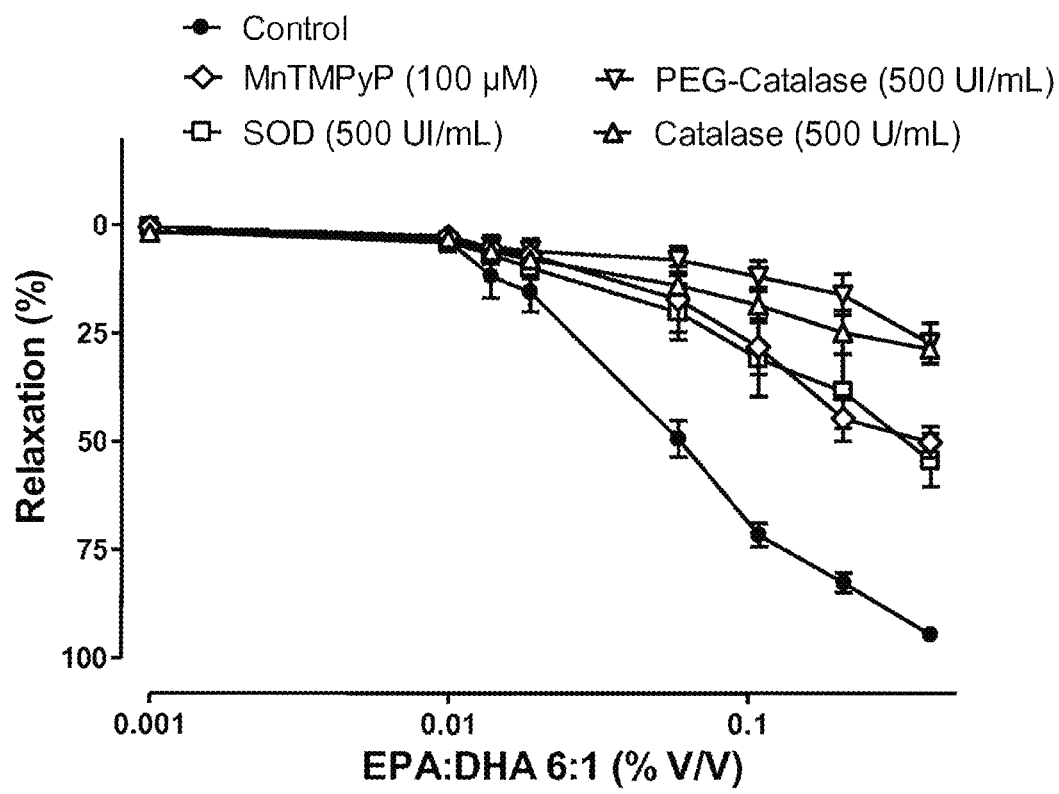
FIG. 7 illustrates the shift in relaxation effect of an EPA:DHA 6:1 product by membrane permeant analogues.

Several studies have shown that relaxations mediated by NO in response to polyphenols derived from grapes involve the redox-sensitive Src/PI3-kinase/Akt pathway (Anselm et al., 2007; Ndiaye et al., 2005). Therefore, it was decided to determine whether this pathway is involved in NO-mediated relaxations to EPA:DHA 6:1. In order to selectively study the NO component, all experiments were conducted in the presence of inhibitors of the EDHF component (Apamin+TRAM 34) and the formation of vasoactive prostanoids (indomethacin). The relaxation induced by EPA:DHA 6:1 was significantly reduced by PP2 (an inhibitor of Src kinase, FIG. 6) and wortmannin (an inhibitor of PI3-kinase, FIG. 6). Furthermore, the relaxations to EPA:DHA 6:1 were shifted to the right by the membrane permeant analog of SOD, MnTMPyP and catalase (PEG-catalase) and by native SOD and catalase (FIG. 7) in a statistically significant amount. Altogether, these findings suggest that Src kinase and the PI3-kinase mediate the stimulatory signal of EPA:DHA 6:1 to eNOS via a redox-sensitive mechanism.

Figure 8A:
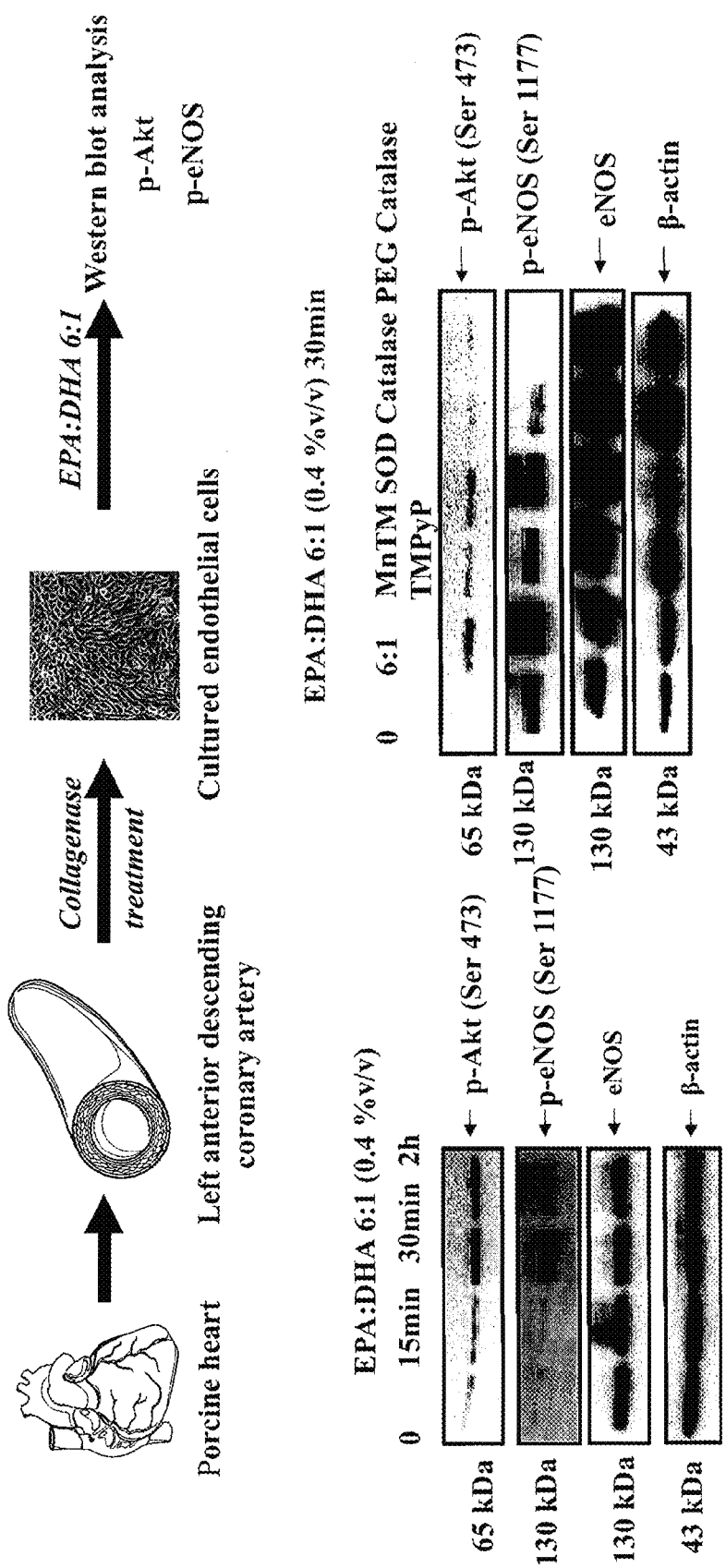
FIG. 8A illustrates the effect EPA:DHA 6:1 has on both Akt and eNOS phosphorylation.
Figure 8B:
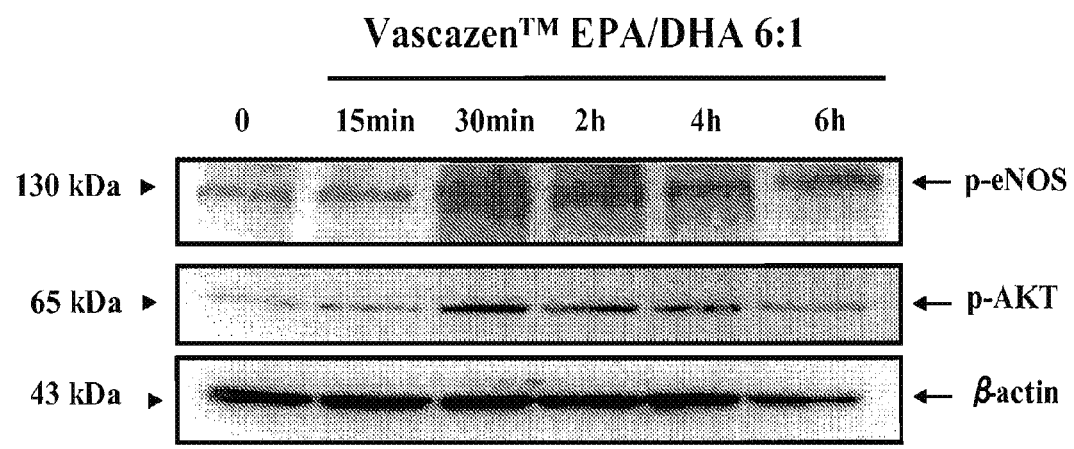
FIG. 8B illustrates Western Blot Data Showing Sustained eNOS Activation of Vascazen at 6 hours at a Concentration of 0.4% and 40 µg of Protein.
Figure 9:
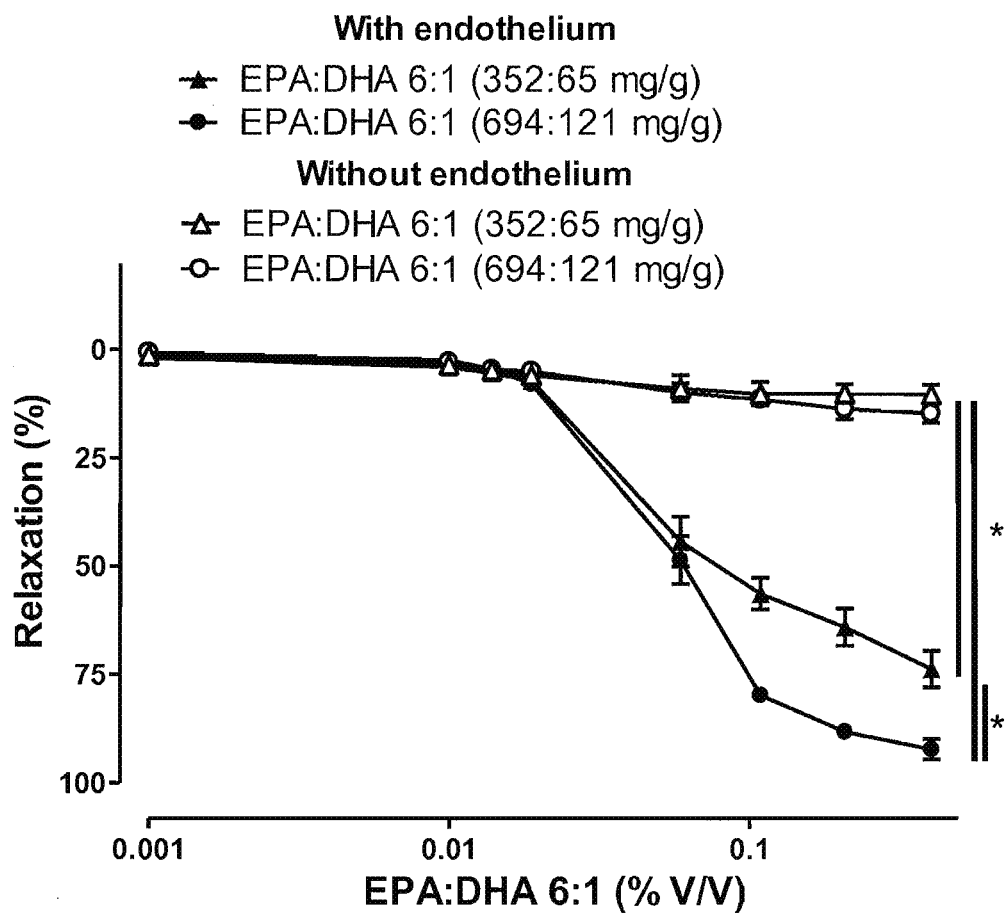
FIG. 9 demonstrates the relation of purity to the sum of EPA+DHA relative to total Omega-3 ratios on the relaxation of coronary artery rings in the presence or absence of endothelium.
Figure 10:
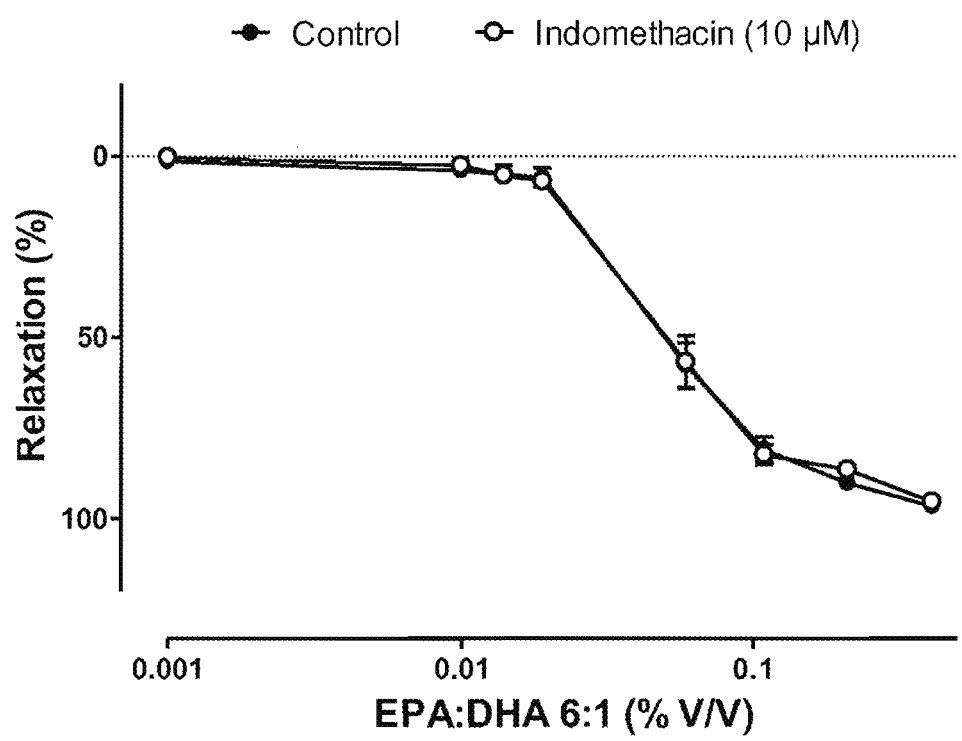
FIG. 10 illustrates that the relaxation effect of the subject EPA:DHA 6:1 formulation is insensitive to the presence of indomethacin.

To obtain direct evidence that EPA:DHA 6:1 is able to activate the PI3-kinase/Akt pathway leading to eNOS activation, cultured coronary artery endothelial cells were exposed to EPA:DHA 6:1 up to 6 hours and the level of phosphorylated Akt and eNOS was determined using Western blot. The data indicate that EPA:DHA 6:1 increased the level of phosphorylation of Akt and eNOS starting at 15 min and that this effect persists until 6 h (FIG. 8A and FIG. 8B). The level of total eNOS expression remained unaffected by the EPA:DHA 6:1 treatment (FIG. 8A). In addition, the stimulatory effect of EPA:DHA 6:1 on phosphorylation of Akt and eNOS was inhibited by MnTMPyP, PEG-catalase and by native SOD and catalase (FIG. 8A). Thus, these data provide direct evidence that EPA:DHA 6:1 activate eNOS via a redox-sensitive mechanism

TABLE 5

Comparative Capsule Contents VASCAZEN ™ vs. German Omega-3 OTC Brands

| Product | Weigt/Capsule (mg) | Omega-3 (mg/%) per Capsule | Vitamin E (mg)/Capsule | Vitamin E (in %)/ Capsule | EPA (mg)/Capsule | DHA (mg)/Capsule | EPA + DHA (in %)/ Capsule |
|---|---|---|---|---|---|---|---|
| ABTEI | 1767 | 390/22.1 | 15 | 0.85 | 230 | 160 | 22 |
| TETESEPT ® | 1350 | 350/25.9 | 15 | 1.1 | 180 | 120 | 22.2 |
| DOPPELHERZ ® | 1300 | 300/23.1 | 12 | 0.92 | 180 | 120 | 23.1 |
| SCHAEBENS VEGETAL | 1450 | 500/34.5 | 10 | 0.07 | n/a (500 mg linolenic acid) | n/a | — |

TABLE 5-continued

Comparative Capsule Contents VASCAZEN ™ vs. German Omega-3 OTC Brands

| Product | Weigt/Capsule (mg) | Omega-3 (mg/%) per Capsule | Vitamin E (mg)/Capsule | Vitamin E (in %)/ Capsule | EPA (mg)/Capsule | DHA (mg)/Capsule | EPA + DHA (in %)/ Capsule |
|---|---|---|---|---|---|---|---|
| SCHAEBENS FISH OIL | 900 | 195/21.67 | 10 | 1.1 | 117 | 78 | 21.7 |
| OPTISANA ® (LIDL) | 708 | 130/18.4 | 6 | 0.85 | 80 | 50 | 18.4 |
| VASCAZEN ™ | 1000 | 900/90% | 2 | 0.2 | 680 | 110 | 79 |

Omega-3 in % signifies total omega-3 in % of total fatty acids as EE (ethyl esters)

Figure 11A:
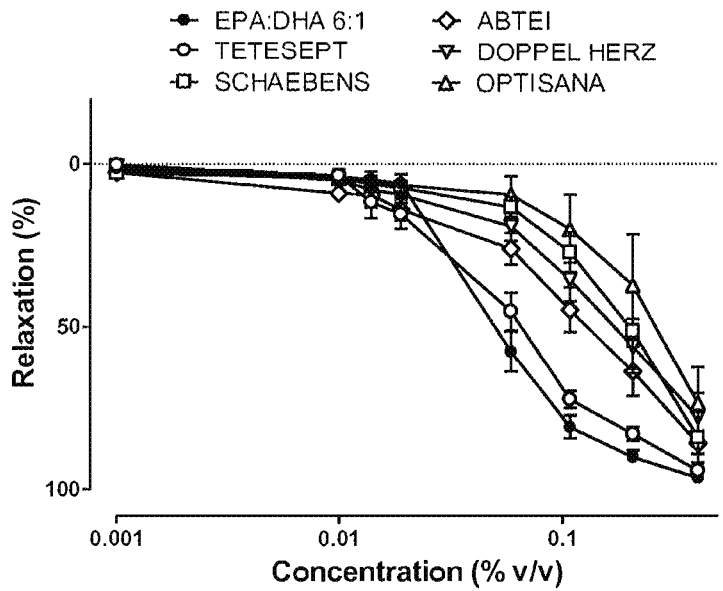
FIG. 11A and FIG. 11B illustrate the indomethacin sensitivity of the relaxation effect of the subject EPA:DHA 6:1 formulation relative to several over the counter Omega-3 products.
Figure 11B:
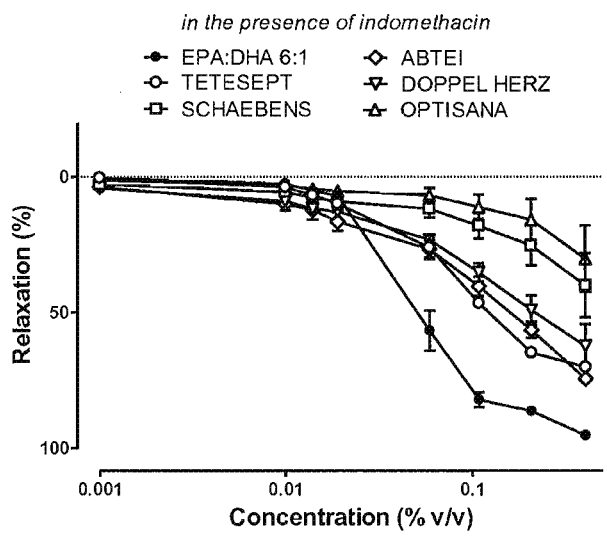
Figure 12:
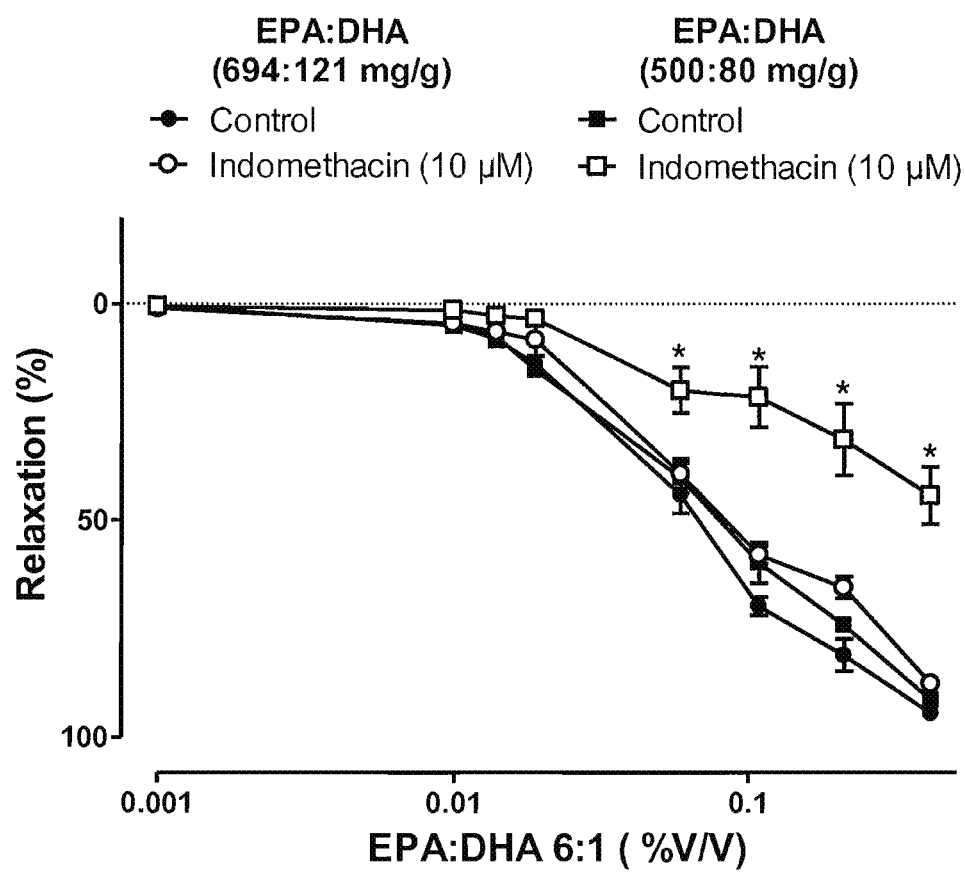
FIG. 12 illustrates the indomethacin sensitivity of the relaxation effect of the EPA:DHA 6:1 formulation relative to a formulation of like ratio containing certain additives.
Figure 13:
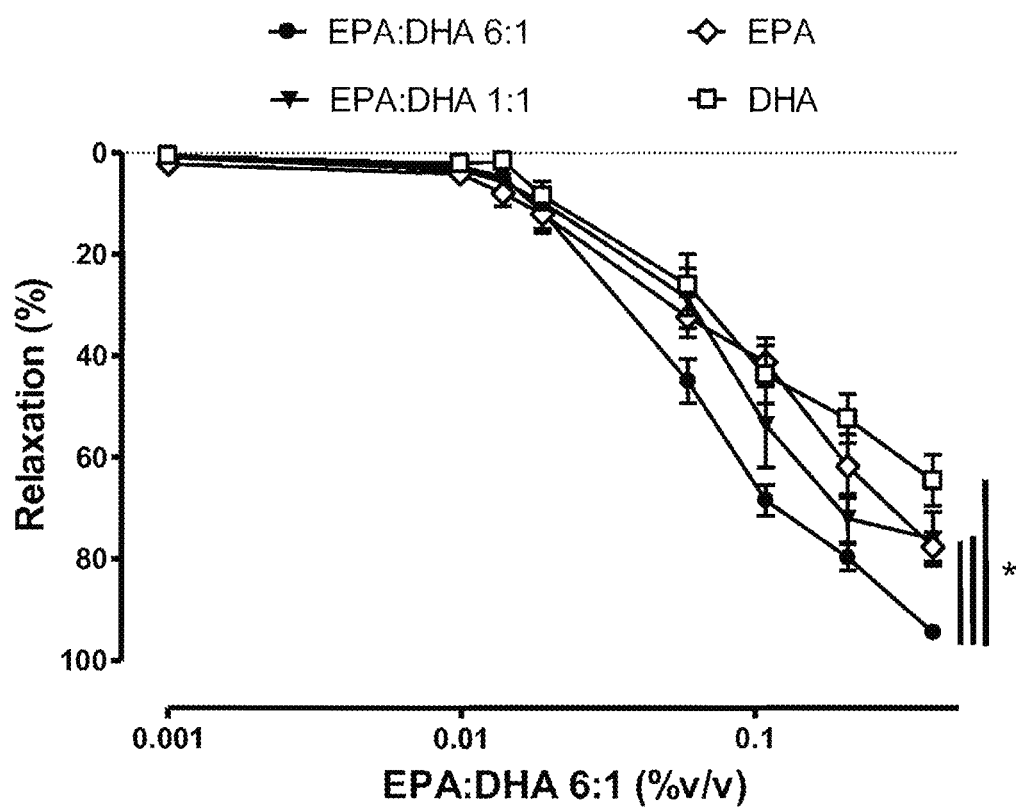
FIG. 13 illustrates the comparative vasorelaxing effect of EPA:DHA 6:1 according to the present invention as compared to EPA:DHA 1:1, EPA alone and DHA alone.

Now referring to FIGS. 9-12, these figures help to illustrate the importance of both the purity of and the presence of additives in the formulation, respectively in providing a maximal relaxation response. For the purpose of this discussion, omega-3 purity was defined as the percentage of the sum of EPA+DHA per capsule. The use of indomethacin as a determinant of the relaxation effect is based upon the following explanation. In some blood vessels vasorelaxing prostanoids such as prostacyclin have been identified as an endotheliun-derived vasorelaxing factor. These vasorelaxing prostanoids are generated from the metabolism of arachidonic acid by cyclooxygenase-1 (COX-1). Indomethacin is an inhibitor of COX-1 and thus will prevent the formation of vasorelaxing prostanoids. The magnitude of the endothelium-dependent relaxation is dependent on the purity of the formulation (FIG. 9) and on the EPA:DHA ratio (FIG. 4). In addition, the EPA:DHA 6:1 formulation caused similar endothelium-dependent relaxation as the OTC Omega-3 product TETESEPT™ with an omega-3 purity (as defined above) of 22.2% as compared to that of the EPA:DHA 6:1 formulation of 75.1% and was much more effective than the other OTC Omega-3s tested (ABTEI LACHSÖL™ 1300, DOPPELHERZ®, SCHAEBENS™ and OPTISANA™ (FIG. 11 A). The endothelium-dependent relaxation induced by VASCAZEN™ (as an example of EPA:DHA 6:1) is not affected by indomethacin at 10 μM. In contrast, the relaxation induced by TETESEPT™ which was similar to that of EPA:DHA 6:1 was significantly reduced by indomethacin (FIGS. 11 A and B). Endothelium-dependent relaxations induced by SCHAEBENS™ and OPTISANA™ were markedly reduced and those to ABTEI™ and DOPPELHERZ® were slightly reduced (FIGS. 11 A and B). These data further indicate that the indomethacin-sensitive relaxation of the OTC Omega-3s cannot be attributed to EPA and DHA nor to its relative concentration ratio but most likely to the presence of additives such as Vitamin E (alpha-tocopherol), see Table 5. Indeed, the vitamin E content of EPA:DHA 6:1 is 0.2% whereas that of OTC Omega-3 formulations varies between 0.85 and 1.1% (Table 5). The importance of the vitamin E additive effect is further suggested by the fact that TETESEPT™ has a more than fivefold higher vitamin E content than that of the EPA:DHA 6:1 formulation. Therefore, the selective inhibitory effect of indomethacin induced upon the TETESEPT™ but not upon the EPA:DHA 6:1 is most likely explained by the more than fivefold higher vitamin E content per capsule. Vitamin E has been shown to cause endothelium-dependent relaxation which is inhibited by indomethacin (Wu et al., J Nutr. 135: 1847-1853, 2005). Both omega-3 purity and additives, contribute to the endothelium-dependent relaxation observed with Omega-3 products. This is further illustrated by comparing the relaxation induced by the EPA:DHA 6:1 formulation to that of the METAGENICS™ EPA-DHA 6:1 formulation. Indeed, the latter is markedly inhibited by indomethacin as compared to the former (FIG. 12). Thus, in the presence of indomethacin, the relaxation observed in the presence of Omega-3 products is clearly dependent on omega-3 purity. These experiments underscore the sustained (greater than 6 hours) vasodilatory effect achieved due to the unique ratio and omega-3 purity of the novel EPA:DHA 6:1 product of the present invention. The combination of the 6:1 ratio coupled with the absence of exogenous impurities in the present invention lead to an indomethacin independent vasodilatory effect when compared to either EPA or DHA alone, EPA:DHA 1:1 or to a 6:1 product which contains exogenous impurities (see FIGS. 4,9,11,12 and 13).

Figure 14:
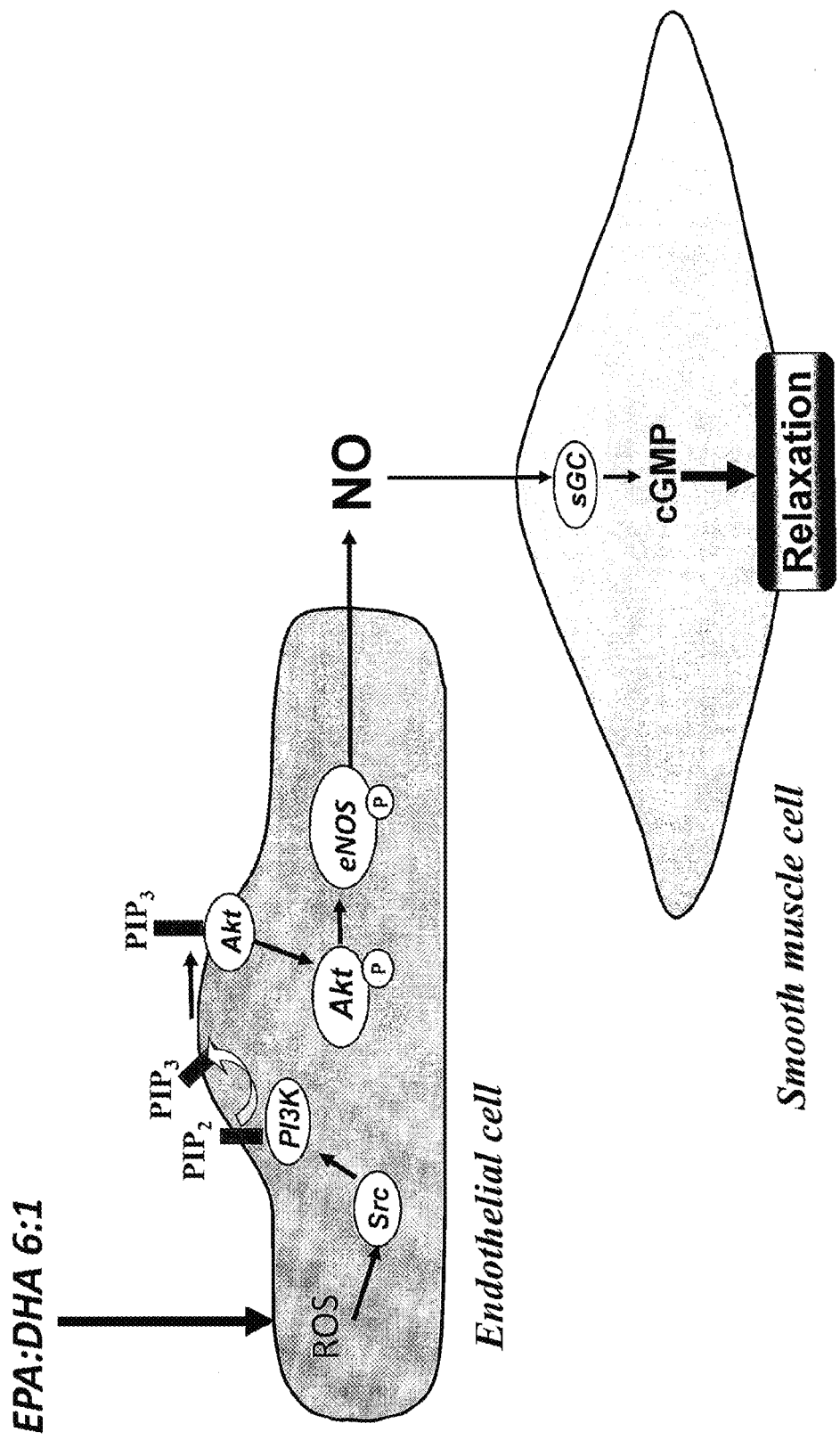
FIG. 14 illustrates the mechanism by which EPA:DHA 6:1 stimulates the endothelial formation of NO via the redox-sensitive activation of the Phosphoinositide 3-Kinase (PI3-Kinase)/Protein Kinase (Akt) pathway.

These findings indicate that omega-3 fatty acid preparations are potent endothelium-dependent vasodilators and that this effect is dependent on the ratio and the omega-3 purity of EPA and DHA within the capsule. They further suggest that omega-3 fatty acids activate eNOS via a redox-sensitive PI3-kinase/Akt pathway leading to changes in the phosphorylation level of eNOS as illustrated in FIG. 14.

Experiment

Physicochemical Characterization and the Kinetic Equilibrium Solubility Comparison Between vascazen™, Oma3™, and Omegabrite™

It is well known that Omega-3 products vary dramatically in their bioavailability. While slight variations in bioavailability are generally not of significance for casual users, whose desire is to ingest these products for maintenance and/or preventive care, a more precise dosing is necessary for therapeutic efficacy. Further studies have indicated the value of ingesting Omega-3 products of relatively high purity. Brhyn et al, "Prostaglandins, Leukotrienes and Essential Fatty Acids", 75(2006) 19-24, demonstrated that the concentration of Omega-3 fatty acids had independent effects on the uptake and outcomes during short-term administration.

The Omega-3 formulation of the instant invention has an EPA/DHA ratio of about 6:1 (5.7:1 to 6.3:1) and greater than 90% purity. As illustrated herein, studies have shown this product to be superior in the treatment of deficiencies in Omega-3, and thereby a superior product for the treatment of cardiovascular disease in this patient population. In order to determine if the demonstrated effects are a result of a novel and intrinsic property of the formulation, or alternatively are a predictable outgrowth of the use of a high purity (greater than 90%) EPA/DHA formulation, that is EPA/DHA ratio dependent, a testing protocol was undertaken utilizing three commercially available Omega-3 ethyl ester products of high purity having differing ratios of EPA/DHA. The products selected were the Omega 3 formulation of the instant invention, VASCAZEN™ (EPA/DHA=about 6:1), OMAX3™ (EPA/DHA=about 4:1), and OMEGABRITE™ (EPA/DHA=about 7:1). Test criteria were designed to elucidate the bioavailability of each formulation.

VASCAZEN™ (EPA/DHA ratio 6:1), OMAX3™ (EPA/DHA ratio 4:1) and OMEGABRITE™ (EPA/DHA ratio 7:1) are commercially available formulated Omega 3 fish oil products, which are generally differentiated by referencing their stated EPA/DHA ratios. Skilled artisans have theorized that differences in their efficacy and bioavailability may be predictable and directly attributable to variations in the empirical EPA/DHA ratio. The present inventors have determined that, surprisingly, this is not the case. On the contrary, the VASCAZEN™ formulation of the instantly disclosed invention has unique and unexpected properties, which do not correlate to the formulation's intrinsic EPA/DHA ratio.

As will be demonstrated in the following experimental analyses, no correlation or linear relationship was found between the varying EPA/DHA ratios of the three different formulations and their intrinsic kinetic solubility profile, which is a measure of their bioavailability. This is an unexpected finding, and may be explained by the fact that these three formulations differ not only by their ratios but, and most importantly, by the uniqueness of their individual qualitative and quantitative components.

Contrary to what a skilled artisan might have predicted based upon alterations in the empirical ratios of EPA/DHA, the instantly disclosed VASCAZEN™ formulation demonstrates unique properties with regard to vasodilation which are counter-intuitive to what might otherwise have been expected by observing only the EPA/DHA ratio.

In order to demonstrate the uniqueness of the poly-unsaturated fatty acid (Omega-3) formulation of the present invention, a physicochemical characterization of Omega-3 formulations was undertaken. This characterization analyzed the thermodynamic Kinetic and Equilibrium solubility of the selected products-VASCAZEN™, available from Pivotal Therapeutics; OMAX3™, available from Prevention Pharmaceuticals; and OMEGABRITE™, available from Omega Natural Science.

At present, bioequivalence of formulated active pharmaceutical ingredients (APIs) is generally done by measuring $C_{Max}$ (Maximum Serum Concentration) and AUC (Area Under the Curve) in accordance with FDA guidelines. These measurements are cumulative measurements of APIs in biological fluids, e.g. urine, plasma, or serum. They do not measure the change in solubilization of varying amounts of APIs over time.

With regard to unformulated APIs, their cumulative solubilization in vitro is determined by either Log P or Log D measurements, reflecting the octanol/water partition coefficients of non-ionized or ionized APIs, respectively. According to established Log P measurement technologies such as ALOGPS, one would expect a linearity of kinetic solubility, based upon $C_{MAX}$ and AUC values, when combining various ratios of pure EPA and DHA.

An alternative technology for measuring bioequivalence and IVIVC (in vitro in vivo correlation) profiles is the SuperSol 1000 system, available from PREVENTOR, μTBC GmbH, Pfungstadt, Germany. The SuperSol 1000 technology is used routinely for investigating differences in solubilization kinetics in a non-cumulative manner, and has become a standard for determining bioequivalence of generic formulated APIs. The sensitivity and specificity of the SuperSol 1000 system enable the identification of differences in solubilization kinetics of formulations with identical or similar molar API/excipient ratios and provides the capability of predicting API pharmacokinetic parameters such as $C_{MAX}$ and AUC.

Detailed Experiment

The products were chosen with the objective of ascertaining a Kinetic solubility comparison between Omega-3-acid ethyl ester capsules of >90% purity containing different EPA/DHA ratios, e.g., Vascazen™ (EPA/DHA ratio 6:1), Omax3™ (EPA/DHA ratio 4:1) and OmegaBrite™ (EPA/DHA ratio 7:1) using thermodynamic kinetic and equilibrium SuperSol 1000 single run screening solubility analysis. Given the extremely low aqueous solubility of Omega-3-acid ethyl esters, an aqueous solution of 2.5% EtOH was used in order to generate a sufficient base line solubility to allow for subsequent kinetic measurements of the solubilization process of each formulation. A sample volume of 350 μl was injected into the measurement column at 37° C.

Definitions

The following parameters were measured:
"Early Kinetic Solubility" or "Early Stage Kinetic Solubility" is understood to refer to the solubility kinetics measured in the time period prior to achieving $C_{MAX}$.
"Late Kinetic Solubility" or "Late Stage Kinetic Solubility" is understood to refer to the solubility kinetics measured subsequent to attaining $C_{MAX}$.
$t_{[MSS]}$ is defined as: Time from start of analysis to Maximum Solubilization Speed (min)
$C_{[MSS]}$ is defined as: Early Kinetic Solubility as expressed as concentration at Maximum Solubilization Speed (mg·l$^{-1}$)
$C_{[Eq]}$ is defined as: Late Kinetic Solubility as expressed as Concentration at Equilibrium Kinetic Solubility (mg·l$^{-1}$)
$t_{[Eq]}$ is defined as: Time from start of analysis to Equilibrium Kinetic Solubility (min)
$\Delta C[C_{[Eq]}-C_{[MSS]}]$ is defined as: Difference in Concentration Between Early and Late Kinetic Solubility as defined above (mg·l$^{-1}$)
$\Delta t[t_{[Eq]}-t_{[MSS]}]$ is defined as: Difference in Time Between Early and Late Kinetic Solubility Endpoints (min)
MSS is defined as: Maximum Solubilization Speed (mg·l$^{-1}$·min$^{-1}$) derived as $C_{[MSS]}/t_{[MSS]}$. This is the earliest kinetic solubility indicator for APIs and unformulated APIs.
ISI is defined as: Intrinsic Solubility Index derived as $\Delta C [C_{Eq}-C_{MSS}]/\Delta t[t_{Eq}-t_{MSS}]$
KSR is defined as: Kinetic Solubility Ratio derived as $C_{[MSS]}/C_{[Eq]}$ and is an in vitro parameter measured by the Supersol 1000 technology which correlates to both $C_{MAX}$ and AUC. In order to compare the sustained release profiles of the three formulations as reflected by AUC in vivo, KSR was measured.

The results of the Supersol 1000 analyses of the VASCAZEN™, OMAX3™ and OMEGABRITE™ formulations are summarized in Table 6.

TABLE 6

| FORMULATION | MSS | $t_{[MSS]}$ | $C_{[MSS]}$ | $C_{[Eq]}$ | $T_{[Eq]}$ | $\Delta C_{[CEq-CMSS]}$ | $\Delta t_{[tEq-tMSS]}$ | ISI | KSR |
|---|---|---|---|---|---|---|---|---|---|
| Vascazen ™ (6:1)* | 323.9 | 2:17 | 323.9 | 513.8 | 8:25 | 189.9 | 6:08 | 31.2 | 0.63 |
| Omax3 ™ (4:1)* | 371.4 | 2:75 | 371.4 | 627.8 | 8:42 | 256.4 | 5:67 | 45.2 | 0.59 |
| OmegaBrite ™ (7:1)* | 200.1 | 1:96 | 200.1 | 372.8 | 8:33 | 172.7 | 6:37 | 27.1 | 0.54 |

*(EPA/DHA Ratio)

Unexpectedly, the values obtained by the SuperSol technology did not evidence any linearity. No correlation or linear relationship was found between the varying EPA/DHA ratios of the three different formulations and their intrinsic kinetic solubility profile. While not wishing to be bound to any particular theory or mechanism of operation, this may be explained by the fact that these three formulations differ not only by their ratios, but also by their individual qualitative and quantitative components.

When comparing equimolar concentrations of varying EPA/DHA ratios of Vascazen™, Omax3™ and OmegaBrite™ the similar ISI values found for Vascazen™ and OmegaBrite™, 31.2 and 27.1, respectively reflect a close EPA/DHA ratio (6:1 vs. 7:1) as opposed to the corresponding ISI of OMAX3™, 45.2, that is significantly higher and demonstrates the more pronounced late solubilization of the latter having an EPA/DHA ratio of 4:1 and a higher composite log P than mixtures with a higher EPA/DHA ratio.

The present results are further interpreted in view of the different log P values of EPA and DHA when incorporated into formulations of pharmaceutical grade as well as the qualitative and quantitative presence of other n-3 and n-6 ingredients present. The lower the Log P value, the higher the cumulative solubility of the API. As reported by Tetko IV et al, ALOGPS, VCC Lab, Drug Discovery Today 10 (2005) Pp. 1497-1500, EPA has both a lower theoretical (6.53) and experimental Log P than DHA (6.83) indicative of a slightly lower lipophilicity and solvation energy. Since the thermodynamic late kinetic solubility kinetics are correlated with log P this signifies that the higher the log P the faster the late solubilization kinetics measured.

The differences in early kinetic solubility between VASCAZEN™ and OMEGABRITE™, however, as reflected by KSR and MSS, are linked neither to log P nor to the ratio itself. Thus, one can only conclude that the enhanced bioavailability of the VASCAZEN™ product is attributable to the other specific fatty acids present, e.g. the qualitative and quantitative nature of other non-EPA and non-DHA n-3 and n-6 ingredients, as further illustrated in Table 7.

Several lots of the VASCAZEN™ formulation, as illustrated in Table 7, were analyzed. Three distinct formulation lots were analyzed in triplicate using different laboratories to yield 9 data points (n=9). This analysis yields numerical ranges, calculated as the average value plus or minus two standard deviations (Avg±2(SD)), which constitute acceptable variations in fatty acid contents for the instant formulation. Formulations within these ranges have been shown to have superior bioavailability, as illustrated by the instant physico-chemical characterization. At the same time, these formulations exhibit a unique and desirable stable and sustained long-acting vasodilatory effect, as has been previously demonstrated herein.

Based upon the data in Table 7, the instantly disclosed composition for treatment or prophylaxis of risk factors for cardiovascular disease (CVD) and protection against sudden death in patients with cardiovascular disease may be defined as a mixture containing omega-3 fatty acids including eicosapentaenoic acid (EPA), docosahexaenoic acid (DHA), and docosapentaenoic acid (DPA) wherein the weight ratio of EPA:DHA is in the range of 5.7:1-6.3:1, and the amount of EPA+DHA in the formulation is about 82.62% to about 87.82% by weight of the total fatty acid content of the formulation, and about 88.26% to about 93.06% by weight of the total omega-3 content of the formulation; the formulation contains from about 93.15% to about 94.87% by weight omega-3 fatty acids, and the sum of EPA, DHA and DPA are from about 85.72% to about 87.82% by weight of the % of total fatty acids in the formulation, and from about 91.38% to about 95.94% by weight of the total % of omega-3 present in the formulation; said formulation contains about 2.53% to about 3.13% by weight of the % of total fatty acids in the formulation of DPA, about 3.04% to about 3.48% by weight of the % of total fatty acids in the formulation of arachidonic acid (AA), and about 3.21% to about 3.45% by weight of the % of total fatty acids in the formulation, of omega-3 fatty acids having 18 carbon atoms, wherein said 18 carbon atom omega-3 fatty acids are alpha-linolenic acid (ALA) and stearidonic acid (SDA). The sum of ALA and SDA is about 3.40% to about 3.68% by weight of the total % of omega-3 present in the formulation.

TABLE 7

| C:unsat-pos | Common Name | AVG (n = 9) | SD | Range = AVG ± 2 SD | | 2 × SD |
|---|---|---|---|---|---|---|
| C18:3 N3 + C18:4 N3 | Alpha Linolenic Acid + Stearidonic Acid | 3.33 | 0.06 | 3.21 | 3.45 | 0.12 |
| C20:4 N6 | Arachidonic Acid | 3.26 | 0.11 | 3.04 | 3.48 | 0.22 |
| C20:5 N3 (EPA) | Eicosspentanoic Acid (EPA) | 72.40 | 0.99 | 70.42 | 74.38 | 1.98 |
| C22:5 N3 (DPA) | Docosapentanoic Acid (n3) DPA | 2.83 | 0.15 | 2.53 | 3.13 | 0.30 |
| C22:6 N3 (DHA) | Docodahexanoic Acid (DHA) | 12.90 | 0.29 | 12.32 | 13.48 | 0.58 |
| | % of total Fatty acid | | | | | |
| | Omega-3 | 94.01 | 0.43 | 93.15 | 94.87 | 0.86 |
| | Omega-6 | 4.42 | 0.38 | 3.66 | 5.18 | 0.76 |
| | % of total Fatty acid | | | | | |
| | EPA → DHA | 85.22 | 1.30 | 82.62 | 87.82 | 2.60 |
| | EPA + DHA + DPA | 88.06 | 1.17 | 85.72 | 90.40 | 2.34 |
| | 18:3 n3- Alpha Linolenic Acid (ALA) | 0.35 | 0.03 | 0.29 | 0.41 | 0.06 |
| | 18:4 n3- Stearidonic acid (SDA) | 2.98 | 0.06 | 2.86 | 3.10 | 0.12 |
| | ALA + SDA | 3.33 | 0.06 | 3.21 | 3.45 | 0.12 |
| | % of Total Omega 3 | | | | | |
| | EPA → DHA | 90.66 | 1.20 | 88.26 | 93.06 | 2.40 |
| | EPA + DHA + DPA | 93.66 | 1.14 | 91.38 | 95.94 | 2.28 |
| | 18:3 n3- Alpha Linolenic Acid (ALA) | 0.37 | 0.04 | 0.29 | 0.45 | 0.08 |
| | 18:4 n3- Stearidonic acid (SDA) | 3.17 | 0.07 | 3.03 | 3.31 | 0.14 |
| | ALA + SDA | 3.54 | 0.07 | 3.40 | 3.68 | 0.14 |

The above data demonstrate that there is no linearity or trend tying the physical characteristics of the test formulations to their EPA/DHA ratios. Furthermore, the data demonstrate a higher bioavailability and solubility for the VASCAZEN™ formulation, which supports the hypothesis that the sustained vasodilation effects achieved by the VASCAZEN™ product are attributable to the unique blend of fatty acids present, and result in a formulation having heretofore unexpected characteristics. The unique blend of fatty acids, which lead to higher bioavailability and solubility, are also thought to be a contributing factor to the formulations ability to stabilize vulnerable plaque.

In order to further determine the benefits of the pharmaceutical composition of the present invention, including a combination of a statin and omega-3 formulation in accordance with the present invention, in the treatment of vulnerable plaque, the composition was administered in accordance with various embodiments.

In some embodiments, the pharmaceutical composition is administered in an amount and for a duration effective to increase plasma EPA levels by at least 100% above pre-treatment levels. In certain embodiments, the pharmaceutical composition is administered in an amount and for a duration effective to increase plasma EPA levels by at least about 200%, 250%, 300%, even at least about 350%, 400%, 450% or at least about 500% above pre-treatment levels. In selected embodiments, the pharmaceutical composition is administered for a time and in an amount effective to increase plasma EPA levels by at least about 550%, 600%, 650%, even at least about 700% above pre-treatment levels.

In various embodiments, the pharmaceutical composition is administered in an amount and for a duration effective to increase plasma DHA levels by at least about 50% above pre-treatment levels. In particular embodiments, the pharmaceutical composition is administered in an amount and for a duration effective to increase plasma DHA levels by at least about 55%, 60%, 65%, 70%, even at least about 75%, 80%, 85%, or 90% above pre-treatment levels.

In a series of embodiments, the pharmaceutical composition is administered in an amount and for a duration effective to increase plasma DPA levels by at least about 50% above pre-treatment levels. In some embodiments, the pharmaceutical composition is administered in an amount and for a duration effective to increase plasma DPA levels by at least about 55%, 60%, 65%, 70%, 75%, even at least about 80%, 85%, 90%, 95%, or 100% above pre-treatment levels. In selected embodiments, the pharmaceutical composition is administered in an amount and for a duration effective to increase plasma DPA levels by at least about 110%, 120%, even at least about 125% above pre-treatment levels.

In a series of embodiments, the pharmaceutical composition is administered in an amount and for a duration effective to reduce arachidonic acid (AA) concentration in plasma by at least about 5% below pre-treatment levels. In certain embodiments, the pharmaceutical composition is administered in an amount and for a duration effective to reduce arachidonic (AA) concentration in plasma by at least about 6%, 7%, 8%, 9%, 10%, even at least about 11%, 12%, 13%, 14%, even at least about 15%, 16%, 17%, 18%, 19%, 20%, or 21%, 22%, 23%, 24% even at least about 25% below pre-treatment levels.

In certain embodiments, the pharmaceutical composition is administered in an amount, and for a duration, effect to reduce plasma arachidonic acid concentration by at least about 25 µg/mL. In some embodiments, the pharmaceutical composition is administered in an amount and for a duration sufficient to reduce plasma AA levels by at least about 50 µg/mL, 55 µg/mL, 60 µg/mL, 65 µg/mL, even at least about 70 µg/mL, 75 µg/mL, 80 µg/mL, 85 µg/mL, 90 µg/mL, even at least about 95 µg/mL or 100 µg/mL.

In certain embodiments, the effective amount is at least about 2 g per day. In various embodiments, the effective amount is at least about 3 g per day. In particular embodiments, the effective amount is at least about 4 g per day. In typical embodiments, the effective amount is about 2 g per day. In certain embodiments, the effective amount is about 4 g per day.

In typical embodiments, the pharmaceutical composition is administered for at least 30 days. In certain embodiments, the pharmaceutical composition is administered for at least 60 days. In particular embodiments, the pharmaceutical composition is administered for at least 90 days, 120 days, 180 days, 240 days, or at least 360 days. In certain embodiments, the pharmaceutical composition is administered indefinitely.

In some embodiments, the pharmaceutical composition is administered daily. In other embodiments, the pharmaceutical composition is administered every other day.

In particular embodiments, the daily dosage of pharmaceutical composition is administered in a single daily dose. In other embodiments, the pharmaceutical composition is administered in divided doses, with the daily dose divided into two administrations, three administrations, or even four administrations, over the course of the day.

In certain embodiments, the pharmaceutical composition is administered with food. In certain embodiments, the pharmaceutical composition is administered with a low fat meal. In other embodiments, the pharmaceutical composition is administered without food. In certain embodiments, the pharmaceutical composition is administered in the fasting state.

An additional study was conducted, authored by Shaikh et al. and entitled "Efficacy Of A Unique Omega-3 Formulation On The Correction Of Nutritional Deficiency And Its Effects On Cardiovascular Disease Risk Factors In A Randomized Controlled VASCAZEN! REVEAL Trial". The results of this study was published in Molecular and Cellular Biochemistry, November 2014, 396(1-2)9-22 (epub September 2014). and are incorporated herein by reference in their entirety.

Data from the REVEAL trial was further analyzed to determine what effects the omega-3 formulation of the present invention might have on the values of various circulating omega-3 fatty acids in a patient population with or without the presence of statins.

Results were analyzed from four patients treated with a combination of a statin and VASCAZEN™ and 16 patients treated with VASCAZEN™ alone.

Patients were analyzed for the percent change in circulating EPA, DHA and DPA from baseline after 8 weeks of treatment.

In the group of patients treated with both a statin and VASCAZEN™ the % EPA change showed an increase of 362.5%; the % DHA change showed an increase of 78.0%; and the % DPA change showed an increase of 130.2%.

In contrast, in the group of patients treated only with VASCAZEN™ the % EPA change showed an increase of 387.6%; the % DHA change showed an increase of 58.4%; and the % DPA change showed an increase of 60.7%.

This data shows that VASCAZEN' in combination with a statin is superior to VASCAZEN™ alone in increasing blood levels of DPA (two fold increase in levels) and a key component in stabilizing vulnerable plaque in cardiovascular patients. This is significant in the reduction of lipid rich plaques in patients suffering from acute coronary syndrome (Amano et al, Impact Of Omega-3 Polyunsaturated Fatty Acids On Coronary Plaque Instability: An Integrated Backscatter Intravascular Ultrasound Study, (Atherosclerosis 218 (2011) 110-116).

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A pharmaceutical formulation provided in therapeutically effective amount for stabilization of vulnerable plaque, consisting of:
   a mixture containing omega-3 fatty acids including eicosapentaenoic acid (EPA), docosahexaenoic acid (DHA), and docosapentaenoic acid (DPA) wherein the weight ratio of EPA:DHA is in the range of 5.7:1-6.3:1; the formulation contains about 90% or more by weight omega-3 fatty acids, and the EPA, DHA and DPA comprise about 82% by weight of the content of the formulation; said formulation contains about 25 mg/g of DPA, about 30 mg/g of arachidonic acid (AA), and about 30 mg/g of one or more omega-3 fatty acids having 18 carbon atoms, wherein said 18 carbon atom omega-3 fatty acid is selected from the group consisting of alpha-linolenic acid (ALA), stearidonic acid (SDA) and combinations thereof; and
   at least one statin wherein the statin comprises at least cerivastatin, atorvastatin, simvastatin, pravastatin, fluvastatin, lovastatin, rosuvastatin, eptastatin, pitavastatin, velostatin, fluindostatin, dalvastain, or pharmaceutically acceptable salts thereof or a combination thereof.

2. A pharmaceutical formulation provided in a therapeutically effective amount for stabilization of vulnerable plaque, consisting of:
   a mixture containing omega-3 fatty acids including eicosapentaenoic acid (EPA), docosahexaenoic acid (DHA), and docosapentaenoic acid (DPA) wherein the weight ratio of EPA:DHA is in the range of 5.7:1-6.3:1, the amount of EPA+DHA in the formulation is about 82.62% to about 87.82% by weight of the total fatty acid content of the formulation, and about 88.26% to about 93.06% by weight of the total omega-3 content of the formulation; the formulation contains from about 93.15% to about 94.87% by weight omega-3 fatty acids; the sum of EPA, DHA and DPA are from about 85.72% to about 87.82% by weight of the total fatty acids in the formulation, and from about 91.38% to about 95.94% by weight of the total omega-3 present in the formulation; said formulation contains about 2.53% to about 3.13% by weight of the total fatty acids in the formulation of DPA, about 3.04% to about 3.48% by weight of the total fatty acids in the formulation of arachidonic acid (AA), and about 3.21% to about 3.45% by weight of the total fatty acids in the formulation, of omega-3 fatty acids having 18 carbon atoms, wherein said 18 carbon atom omega-3 fatty acids are alpha-linolenic acid (ALA) and stearidonic acid (SDA); and wherein the sum of ALA and SDA is about 3.40% to about 3.68% by weight of the total omega-3 present in the formulation; and
   at least one statin wherein the statin comprises at least cerivastatin, atorvastatin, simvastatin, pravastatin, fluvastatin, lovastatin, rosuvastatin, eptastatin, pitavastatin, velostatin, fluindostatin, dalvastain, or pharmaceutically acceptable salts thereof or a combination thereof.

3. The formulation in accordance with claim 1, wherein the omega-3 fatty acids are in the form of ethyl esters and pharmaceutically acceptable salts thereof.

4. The formulation in accordance with claim 1, wherein the omega-3 fatty acids are in the form of triglycerides and pharmaceutically acceptable salts thereof.

5. The formulation in accordance with claim 1, wherein the omega-3 fatty acids are in the form of phospholipids and pharmaceutically acceptable salts thereof.

6. The formulation in accordance with claim 1, in a unit dosage form comprising from about 645 to about 715 mg/gm EPA from about 105 to about 115 mg/gm, DHA and from about 22 to about 28 mg/gm, DPA.

7. The formulation in accordance with claim 1, in a unit dosage form comprising at least 680 mg EPA, at least 110 mg DHA and at least 25 mg DPA.

8. The formulation in accordance with claim 6, wherein the formulation additionally comprises a stabilizer.

9. The formulation in accordance with claim 8, wherein the stabilizer is tocopherol in an amount of about 0.2% per weight of the total formulation.

10. The formulation in accordance with claim 6, wherein the unit dosage form may comprise tablets, capsules, pills, powders, granules, and oral solutions or suspensions.

11. The formulation in accordance with claim 10, wherein the unit dosage form is a gel or liquid capsule.

12. A process for the stabilization of vulnerable plaque comprising:
   identifying a patient population that exhibits deficiencies in omega-3 fatty acids; and
   administering to said patient population a formulation in accordance with claim 1; whereby a therapeutic effect is achieved.

13. A process for the stabilization of vulnerable plaque comprising:
   identifying a patient population that exhibits deficiencies in omega-3 fatty acids; and
   administering to said patient population a formulation in accordance with claim 2; whereby a therapeutic effect is achieved.

* * * * *